(12) United States Patent
DiPerna

(10) Patent No.: US 11,135,354 B2
(45) Date of Patent: Oct. 5, 2021

(54) FLUID DELIVERY PUMP

(71) Applicant: Quasuras, Inc., Escondido, CA (US)

(72) Inventor: Paul Mario DiPerna, Cardiff, CA (US)

(73) Assignee: QUASURAS, INC., Escondido, CA (US)

( * ) Notice: Subject to any disclaimer, the term of this patent is extended or adjusted under 35 U.S.C. 154(b) by 974 days.

(21) Appl. No.: 15/122,132

(22) PCT Filed: Mar. 3, 2015

(86) PCT No.: PCT/US2015/018525
§ 371 (c)(1),
(2) Date: Aug. 26, 2016

(87) PCT Pub. No.: WO2015/134526
PCT Pub. Date: Sep. 11, 2015

(65) Prior Publication Data
US 2016/0361489 A1 Dec. 15, 2016

Related U.S. Application Data

(60) Provisional application No. 61/947,032, filed on Mar. 3, 2014.

(51) Int. Cl.
| *A61M 5/142* | (2006.01) |
| *A61M 5/168* | (2006.01) |
| *A61M 5/145* | (2006.01) |

(52) U.S. Cl.
CPC .... *A61M 5/14216* (2013.01); *A61M 5/14224* (2013.01); *A61M 5/16809* (2013.01);
(Continued)

(58) Field of Classification Search
CPC .. A61M 5/1407–1409; A61M 5/16827; A61M 5/19; A61M 5/20; A61M 5/2066;
(Continued)

(56) References Cited

U.S. PATENT DOCUMENTS

| 4,594,058 A | 6/1986 | Fischell |
| 5,399,168 A | 3/1995 | Wadsworth et al. |

(Continued)

FOREIGN PATENT DOCUMENTS

| EP | 3165247 | 5/2017 |
| WO | WO 15/134526 | 9/2015 |

(Continued)

OTHER PUBLICATIONS

International Search Report and Written Opinion dated Oct. 18, 2018 in International Application No. PCT/US2018/40944, filed: Jul. 5, 2018 and published as: WO/2019/010324 on Jan. 10, 2019.
(Continued)

*Primary Examiner* — William R Carpenter
*Assistant Examiner* — Larry R. Wilson
(74) *Attorney, Agent, or Firm* — Schmeiser, Olsen & Watts LLP

(57) ABSTRACT

A pump controllably moves a small quantity of fluid from a fluid chamber to an outlet port with a small inexpensive actuator powered for a very short amount of time, thereby optimizing cost, size, and battery efficiency. Multiple pumps can be housed in a single enclosure, allowing multiple drugs to each be injected through a single cannula or needle.

9 Claims, 23 Drawing Sheets

(52) U.S. Cl.
CPC ............. *A61M 2005/14506* (2013.01); *A61M 2205/3344* (2013.01); *A61M 2205/3368* (2013.01); *A61M 2205/8212* (2013.01); *A61M 2206/22* (2013.01)

(58) Field of Classification Search
CPC ............ A61M 5/14216; A61M 5/1422; A61M 5/14224; A61M 5/145; A61M 5/1452; A61M 5/14526; A61M 5/1454; A61M 5/14546; A61M 5/14586; A61M 5/152; A61M 5/168; A61M 5/16804; A61M 5/16809; A61M 2005/14506; A61M 2005/14533; A61M 5/14506; F04B 1/124; F04B 1/22; F04B 9/02; F04B 9/025; F04B 9/06; F04B 13/00; F04B 13/02; F04B 17/03–048; F04B 43/0018
See application file for complete search history.

(56) References Cited

U.S. PATENT DOCUMENTS

| | | | |
|---|---|---|---|
| 5,573,515 A * | 11/1996 | Wilson | A61M 5/14216 604/236 |
| 6,186,982 B1 | 2/2001 | Gross et al. | |
| 6,620,138 B1 * | 9/2003 | Marrgi | A61M 5/1408 604/110 |
| 8,056,582 B2 | 11/2011 | DiPerna | |
| 8,167,581 B2 | 5/2012 | Schneeberger et al. | |
| 8,298,184 B2 | 10/2012 | DiPerna et al. | |
| 8,408,421 B2 | 4/2013 | DiPerna | |
| 8,425,493 B2 | 4/2013 | Lord et al. | |
| 8,448,824 B2 | 5/2013 | DiPerna | |
| 8,545,440 B2 * | 10/2013 | Patrick | A61M 5/1452 604/83 |
| 8,573,027 B2 | 11/2013 | Rosinko et al. | |
| 8,926,561 B2 | 1/2015 | Verhoef et al. | |
| 8,986,253 B2 | 3/2015 | DiPerna | |
| 9,211,377 B2 | 12/2015 | DiPerna et al. | |
| 9,250,106 B2 | 2/2016 | Rosinko et al. | |
| 10,010,674 B2 | 7/2018 | Rosinko et al. | |
| 2002/0004643 A1 * | 1/2002 | Carmel | A61M 5/24 604/86 |
| 2003/0086799 A1 * | 5/2003 | Falk | F04B 17/042 417/417 |
| 2004/0257413 A1 | 12/2004 | Anderson et al. | |
| 2005/0119611 A1 | 6/2005 | Marano-Ford et al. | |
| 2008/0051716 A1 * | 2/2008 | Stutz | A61M 5/1413 604/151 |
| 2008/0092969 A1 | 4/2008 | DiPerna | |
| 2010/0145303 A1 * | 6/2010 | Yodfat | A61M 5/1723 604/506 |
| 2010/0232992 A1 | 9/2010 | Gray | |
| 2011/0021993 A1 | 1/2011 | Bar-Haim et al. | |
| 2011/0186177 A1 | 8/2011 | Lanier, Jr. et al. | |
| 2013/0055889 A1 | 3/2013 | Herz et al. | |
| 2013/0150824 A1 | 6/2013 | Estes et al. | |
| 2015/0273201 A1 | 10/2015 | Tallarida et al. | |
| 2015/0290445 A1 | 10/2015 | Powers et al. | |
| 2016/0129178 A1 | 5/2016 | Askarinya et al. | |
| 2016/0361489 A1 | 12/2016 | DiPerna | |
| 2017/0128709 A1 | 5/2017 | Chen | |
| 2019/0009023 A1 | 1/2019 | DiPerna et al. | |
| 2020/0030529 A1 | 1/2020 | Di Perna et al. | |

FOREIGN PATENT DOCUMENTS

| | | |
|---|---|---|
| WO | WO 17/194074 | 11/2017 |
| WO | WO 19/010324 | 1/2019 |

OTHER PUBLICATIONS

International Search Report and Written Opinion dated Oct. 4, 2019 in International Application No. PCT/US2019/43146 filed: Jul. 24, 2019.
Office Action dated Nov. 16, 2020 in U.S. Appl. No. 16/028,256, filed Jul. 5, 2018 and published as: 2019/0009023 on Jan. 1, 2019.
Supplementary European Search Report dated Mar. 12, 2021 in European Patent Application No. EP 18828123.2 filed: Jul. 5, 2018.
Invitation to Pay Additional Fees dated Feb. 23, 2021 in International Application No. PCT/US2020/63152 filed: Dec. 3, 2020.
International Preliminary Report on Patentability dated Jan. 26, 2021 in International Application No. PCT/US2019/43146 filed: Jul. 24, 2019.
WIPO, U.S. International Search Authority, International Search Report and Written Opinion dated Jul. 31, 2015 in International Patent Application No. PCT/US2015/018525, 10 pages.
Non-Final Office Action dated May 28, 2021 in U.S. Appl. No. 16/028,256, filed Jul. 5, 2018 and published as: 2019/0009023 dated Jan. 1, 2019.

* cited by examiner

FLUID DELIVERY PUMP

RELATED APPLICATIONS

This application is the U.S. National Phase of and claims priority to International Patent Application No. PCT/US2015/018525, International Filing Date Mar. 3, 2015, entitled Fluid Delivery Pump, which claims priority to U.S. Provisional Application Ser. No. 61/947,032 filed Mar. 3, 2014 entitled Fluid Delivery Damping and Delivery Pump, both of which are hereby incorporated herein by reference in their entireties.

BACKGROUND OF THE INVENTION

Insulin pumps are medical devices used for the administration of insulin in the treatment of diabetes, which is known as continuous subcutaneous insulin infusion therapy. Typically, insulin pumps include a pump mechanism, a disposable reservoir for insulin, and a disposable infusion set (e.g., a cannula for insertion under the user's skin).

In an attempt to increase battery efficiency and safety, a variety of different pump mechanisms have been contemplated in battery powered insulin pumps. For example, such pump mechanism include servomotors with gear trains; nitinol wires that deform when electrically stimulated; heated wax that changes volume or actuates a check valve, and MEMS valves whose diaphragm motion open and close check valves. These methods however typically require complex, large, and expensive mechanical arrangements, as well as having substantial power consumption, requiring a large battery and/or frequent recharging.

SUMMARY OF THE INVENTION

In one aspect of the present invention, a pump controllably moves a small quantity of fluid from a fluid chamber to an outlet port with a small inexpensive actuator powered for a very short amount of time, thereby optimizing cost, size, and battery efficiency.

In another aspect of the present invention, the pump includes a fail-safe position such that component failure will not result in free flow between the fluid chamber and the patient.

Another aspect of the present invention includes a method of pumping a fluid in which a pulse of a device such as an electrical solenoid pushes on a piston to controllably move a small quantity of fluid by hydraulically filling a pressurized delivery chamber. The delivery chamber slowly dispenses the fluid by adding a restriction to the flow out of the outlet port to dampen the fluid flow rate between actuations to prevent sudden spikes of liquid.

Another aspect of the present invention includes a pump enclosure having multiple pump mechanisms, which can each be configured to pump a different drug to a patient.

Yet another aspect of the present invention includes a method of delivering different drugs to a patient from a single pump enclosure.

Yet another aspect of the present invention includes measuring sensor data from within an air chamber open to the atmosphere within a pump enclosure and determining a volume of fluid remaining in a fluid chamber.

Another aspect of the present invention includes calibrating a pump enclosure for measuring an accurate volume of fluid in a fluid chamber.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 26A-30 illustrate various options of materials within fluid chambers of the pump enclosure according to FIGS. 17-26.

DESCRIPTION OF EMBODIMENTS

Figure 1A:
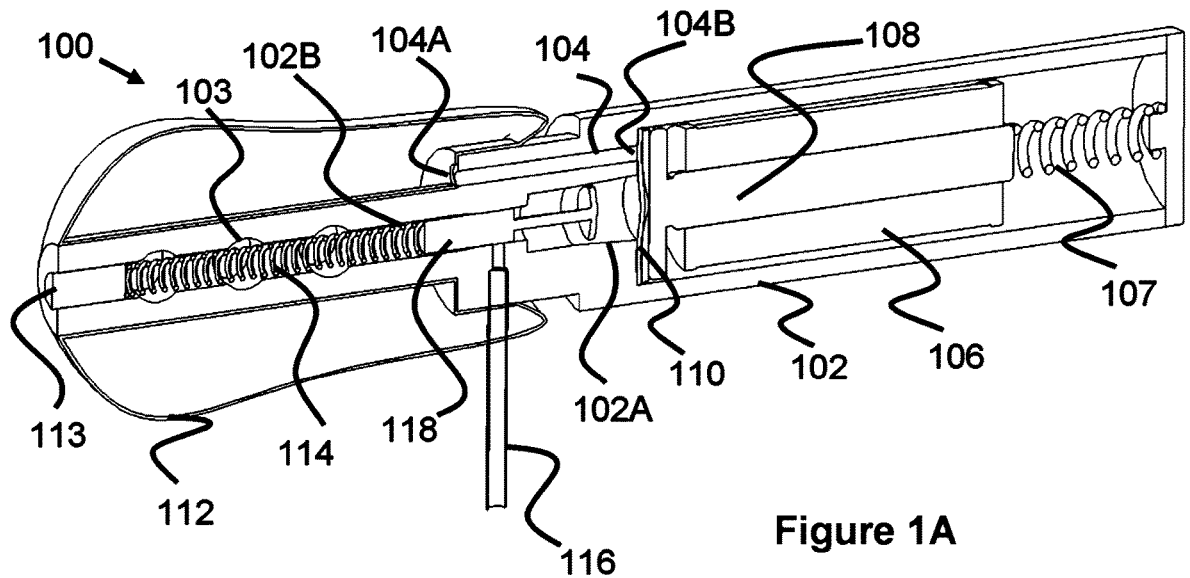
FIGS. 1A-5 illustrate one embodiment of a fluid pump according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Pump Mechanism and Operation

One aspect of the present invention is directed to a pump mechanism and method of use. Specifically, a displacement mechanism is used deliver small quantities of fluid (e.g., insulin) to a patient or to another pumping application. While the present specification primarily describes a solenoid as the displacement mechanism, it should be understood that a number of other devices can also be used, such as a motor, electromagnet, cam actuators, ultrasonic motors, magnets with shielding, Nitinol wire phase change materials, expanding/contracting materials, or similar devices.

FIGS. 1A-5 discloses one embodiment of a pump mechanism 100 that is actuated by a solenoid 106. When the solenoid 106 is operated, fluid (e.g., insulin) from a fluid chamber 112 is pumped into the input port 104A, through input lumen 104, and ultimately out the output port 116.

The solenoid 106 is preferably located within a chamber of a pump housing 102 and, when activated, moves a plunger 108 against a compressible elastomer film or flexible sheet 110. The film 110 is preferably connected around or near its outer edges and is fitted to have slack (i.e., is not pulled tight), allowing the film 110 to deform or bend. In this respect, when the plunger 108 is extended (i.e., moved to the left), the film 110 is pressed against an end port 104B of the input passage 104, closing off the port 104B and preventing any further liquid to enter the pump 100.

Figure 1B:
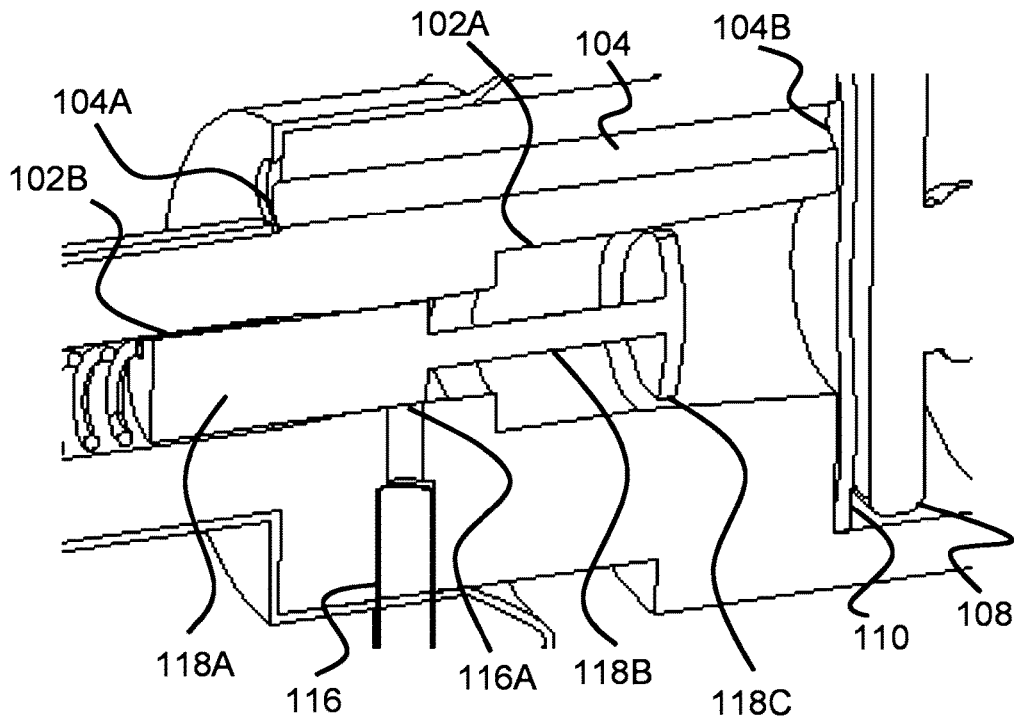

The pump 100 also includes a delivery piston 118 that moves laterally between a larger diameter pump chamber 102A and a smaller diameter pump chamber 102B (seen best in FIG. 1B). The delivery piston 118 includes a cylindrical portion 118A which has diameter that is slightly smaller than the chamber 102B, allowing the cylindrical portion 118A to slide within the chamber 102B. A disk portion 118C is connected to the cylindrical portion by an elongated connection portion 118B, and has a diameter that is slightly smaller than the chamber 102A.

The piston 118 is biased towards the solenoid 106 by a spring 114. The spring 114 is preferably connected to the cylindrical portion 118A and to a location left of the piston, such as the septum 113 or to the wall of the chamber 102B. Since the fast action of the on/off cycle of a solenoid 106 (or similar actuator mechanism) can delivery fluid faster than the patient's tissue can absorb, creates sheer forces on the fluid molecules (e.g., insulin) potentially disrupting their efficacy, and can potentially injure the patient at the injection site, the spring helps dampen the solenoid force. Specifically, as the solenoid causes the delivery piston 118 to move to the left, the spring 114 helps reduce the speed of the piston 118 to create a more gentle movement, as well as stores some of the energy create by the solenoid 106. While a spring 114 is described, it should be understood that a variety of different dampening mechanisms are possible, such as magnetic dampening mechanisms and elastomeric members.

To allow movement of the delivery piston 118 and injection of fluid via the septum 113, the smaller diameter pump chamber 102B includes one or more fluid return ports 103 (e.g., 3 or 6 ports), which connect the pump chamber 102B with the fluid chamber 112.

With regard to the operation of the pump 100, FIGS. 1A and 1B illustrates the pump in a neutral position in which the delivery position 118 covers the entrance 116A to the output port 116.

Figure 2:
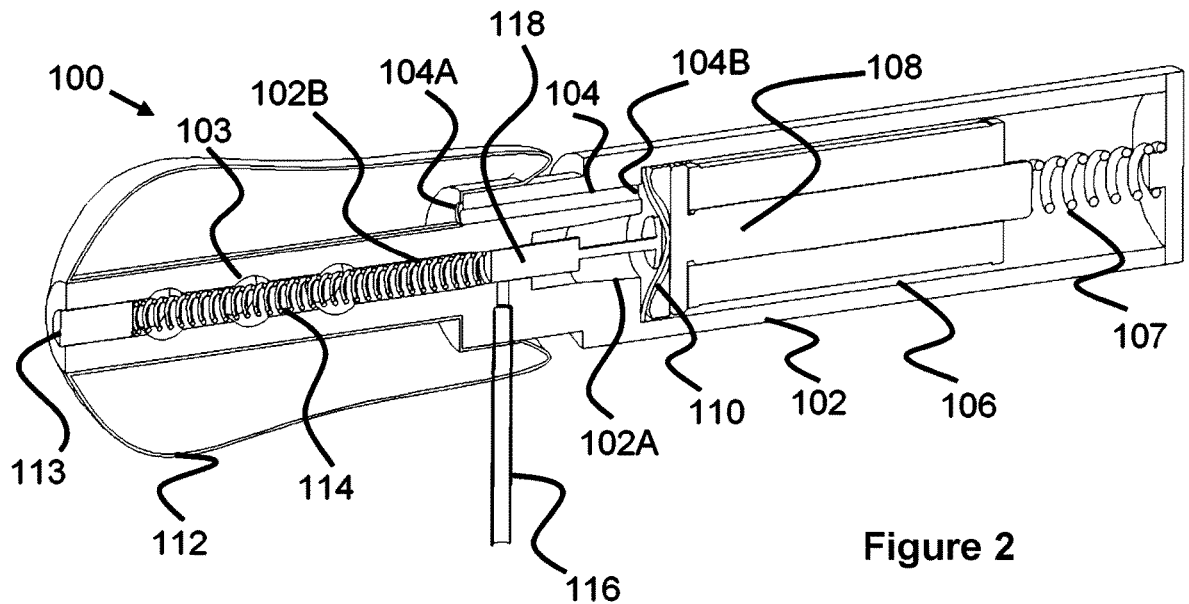

Turning to FIG. 2, power is applied to the solenoid 106, causing the plunger 108 move to the right, against the plunger return spring 107. The delivery piston 118 also moves to the right, maintaining the output port 116 in a blocked or closed configuration and pressing against the film 110 so as to open the input lumen 104. In this respect, fluid from the fluid chamber 112 passes into input port 104A, along input passage 104, out the end port 104B, and into the larger diameter chamber 102A.

Figure 3:
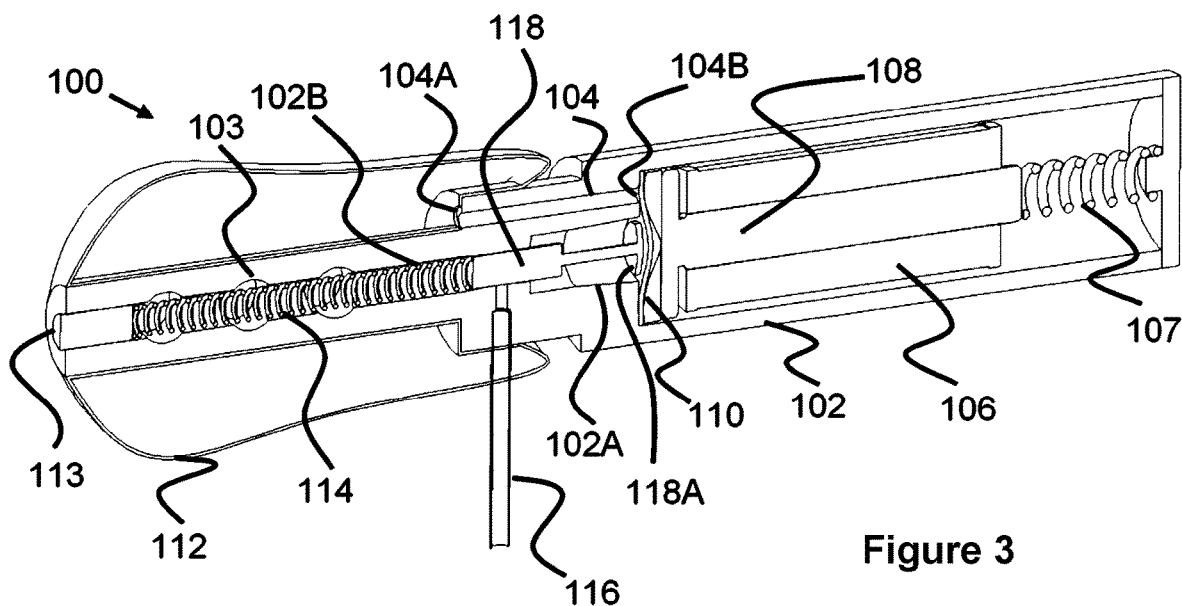

Once the larger diameter chamber 102A has filled with fluid, the solenoid 106 is powered off, allowing the plunger release spring 107 to begin moving fluid towards the left of the pump 100, thereby causing the fluid to move the piston 118 to the left, as seen in FIG. 3. As such, the end port 104B becomes covered or blocked by the film 110, preventing further passage of fluid through the input passage into the chamber 102A.

Figure 4A:
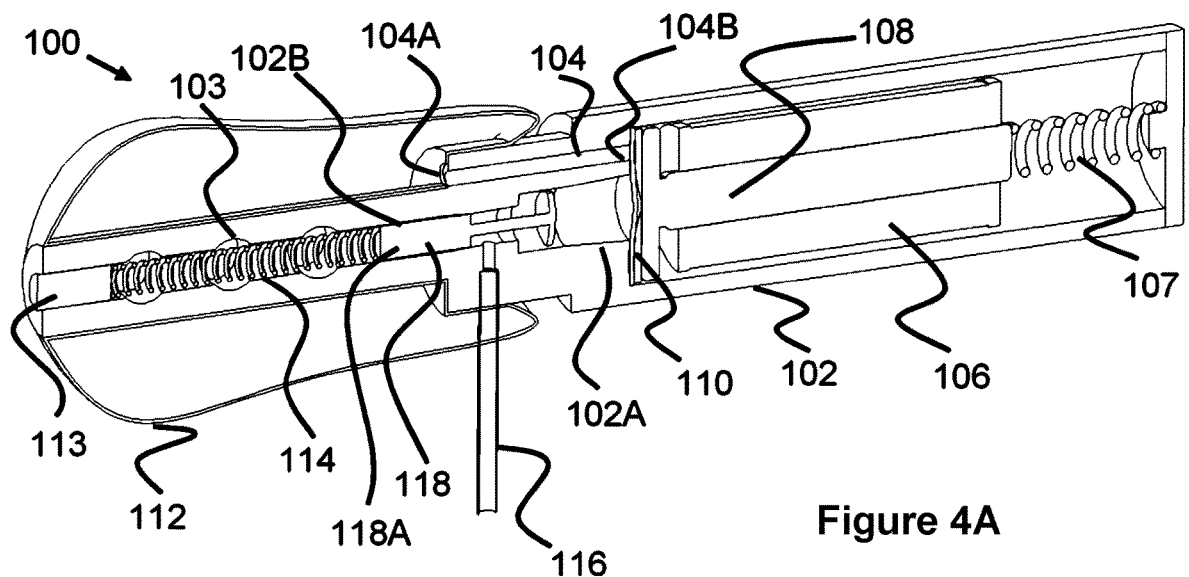
Figure 4B:
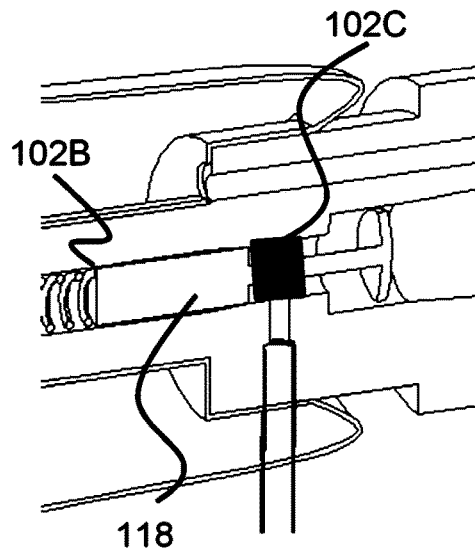

As seen in FIG. 4A, the continued movement of the plunger 108 to the left against the film 110, causing the fluid in the chamber 102A to press against the delivery piston 118, moving the piston 118 further to the left. At this position, the cylindrical portion 118A no longer blocks the output port 116 and a portion of the fluid in the smaller diameter chamber 102B (e.g., portion 102C in FIG. 4B). In other words, the entire contents of both chambers 102A and 102B do not empty out of the output port 116; instead only a fraction of that fluid is displaced. Additionally, the piston 118 has compressed against the spring 114, storing some of the energy imparted via the solenoid 106 and displacing some of the fluid on the left side of the piston 118 out the fluid return ports 103.

It should be understood that the amount and rate of fluid leaving the chamber 102B in this position can be controlled by a number of factors. For example, the diameter and length of the output port 116 can both be increased or decreased to adjust an amount and/or rate of displaced fluid per cycle. Other factors may also influence this, such as the compressibility of the springs 114 and 107, the size of the chambers 102A and 102B, the diameter holding the fluid in the film, and the strength and actuation time/speed of the solenoid 106.

Figure 5:
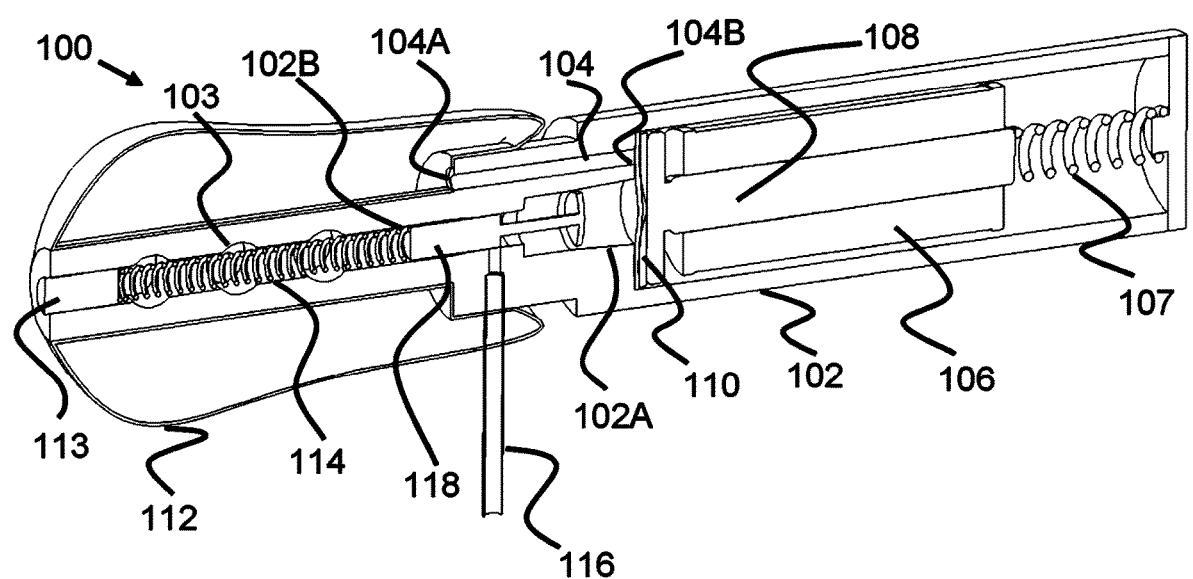

Referring to FIG. 5, with a portion of the fluid displaced, the spring 114 begins to push back the piston 118, closing the output port 116 and returning to a neutral (i.e., nonmoving position). In this position, both the output port 116 and the end port 104 of the input passage 104 are closed. In this respect, if the solenoid 106 or other components controlling the solenoid 106 break, or if the piston sticks, the pump will not allow constant flow of insulin through the pump 100 and into the patient.

FIGS. 6A-11B illustrate another embodiment of a pump 130 that is constructed and operates in a generally similar manner to the previously described pump 100. However, instead of single piston and a film, the present pump 130 includes a solid, cylindrical delivery piston 132, a tubular fill piston 134, and a cylindrical refill piston 136.

The cylindrical delivery piston 132 is preferably sized slightly smaller in diameter than smaller diameter chamber 102B and moves laterally to selectively block the output port 116. The tubular fill piston 134 is sized slightly smaller in diameter than the larger chamber 102A and moves laterally to selectively open and close the input passage 104. The tubular fill piston 134 also includes a passage therethrough in which the cylindrical refill piston 136 slides during operation, creating a small refill chamber.

Figure 6A:
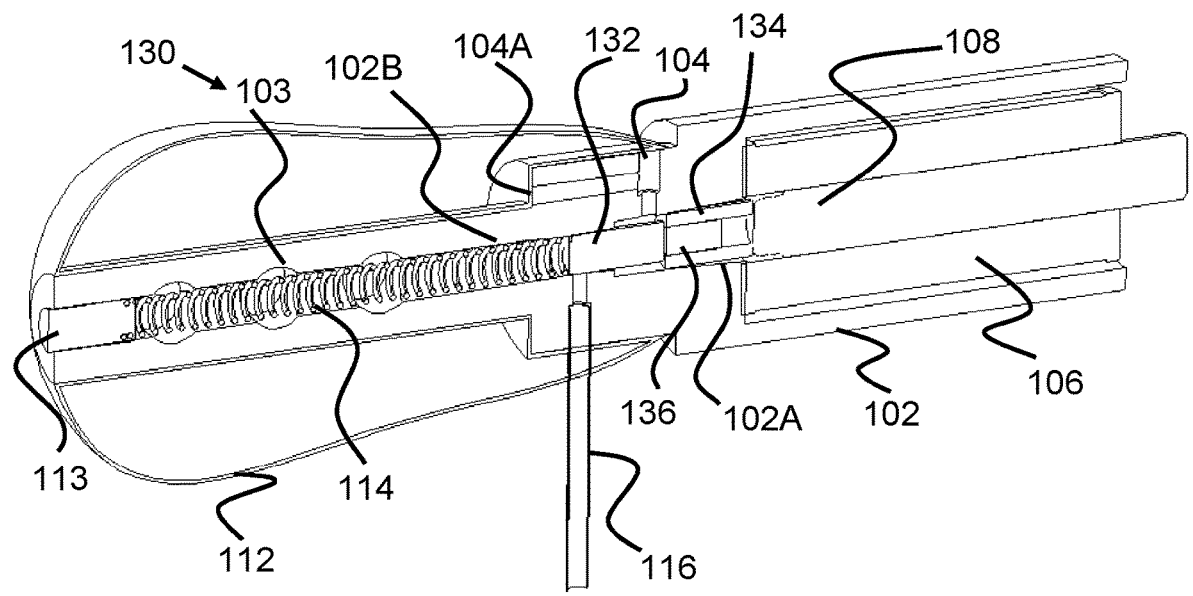
FIGS. 6A-11B illustrate another embodiment of a fluid pump according to the present invention.
Figure 6B:
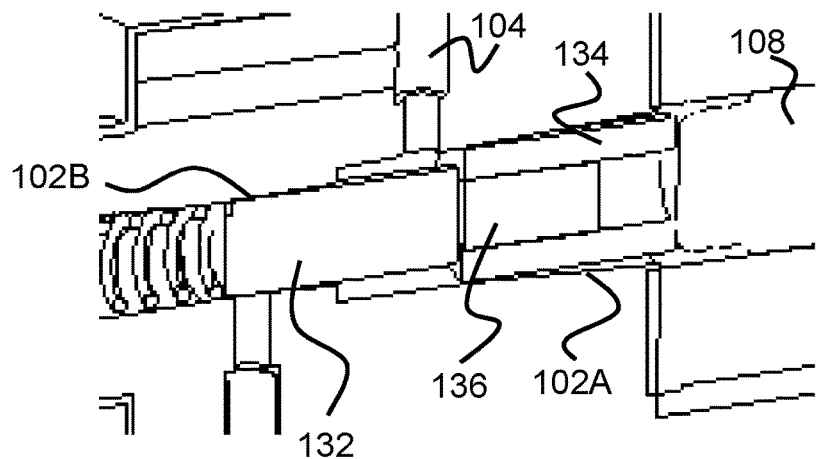

FIGS. 6A and 6B illustrate the pump 130 in a neutral position in which neither the solenoid 106, nor the spring 114 are actively creating motion of the components within the pump 130. The delivery piston 132 can be seen closing off the delivery port 116, preventing fluid from passing to the patient. The fill piston 134 can be seen moved to the right, allowing fluid to enter from the input passage into the area around the delivery piston 132 within the larger chamber 102A.

Figure 7A:
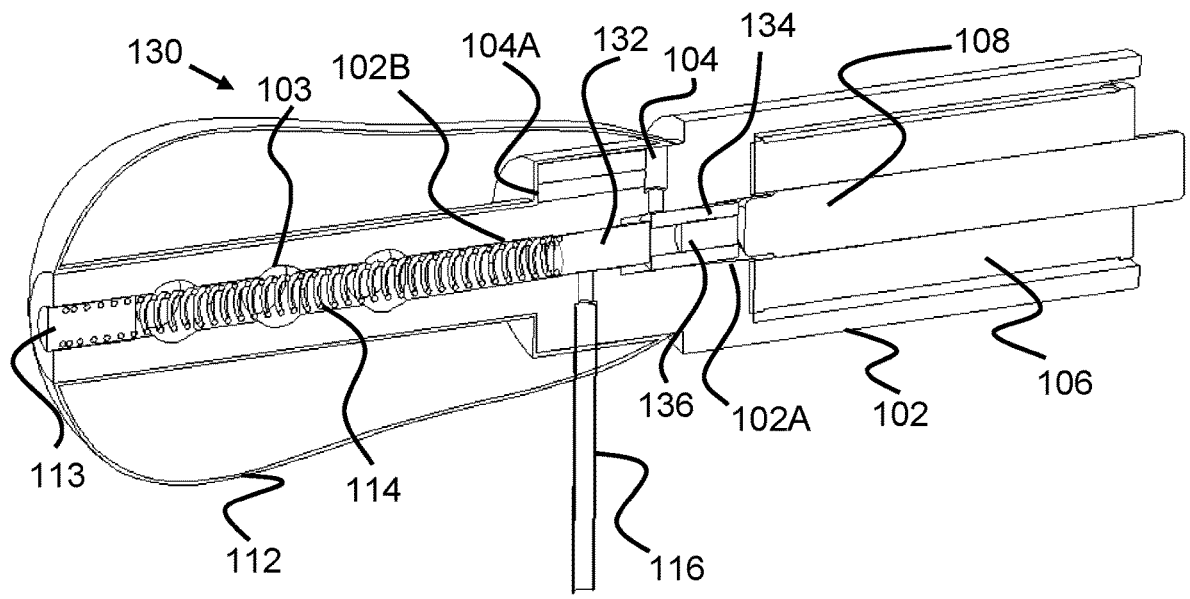
Figure 7B:
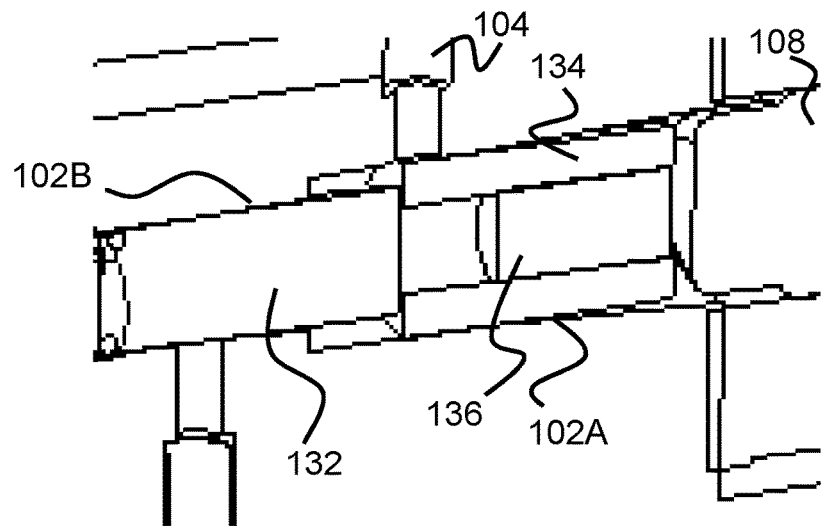

In FIGS. 7A and 7B, the solenoid 106 is actuated (i.e., power is applied), causing the plunger 108 to move to the left. As the plunger moves 108, pressure builds within the chamber 102A, causing the refill piston 136 to push back, to the right. As the fill piston 134 continues to move to the left, it closes of the input port 104, creating a small, somewhat pressurized chamber of fluid within the fill piston 134.

Figure 8A:
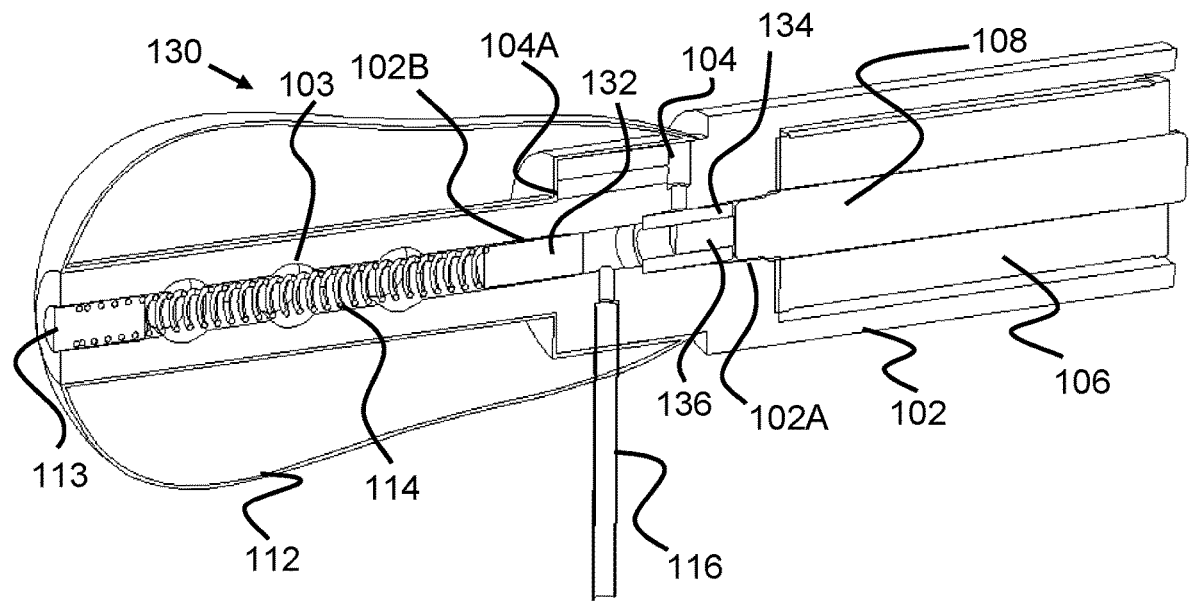
Figure 8B:
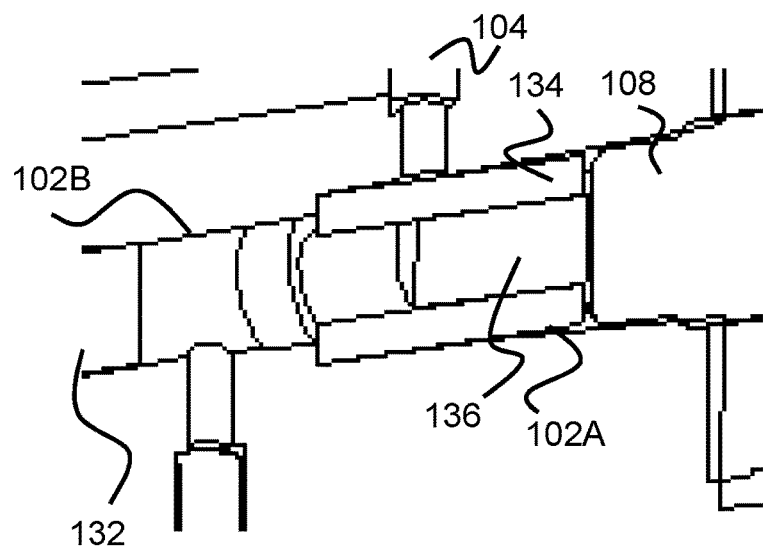

As seen in FIGS. 8A and 8B, the plunger 108 continues to move left, moving with it the fill piston 134, the refill piston 136 and the delivery piston 132. In this position, the delivery piston 132 has moved far enough to the right so as to open output port 116, thereby allowing some of the fluid to be discharged from the pump 130.

Figure 9A:
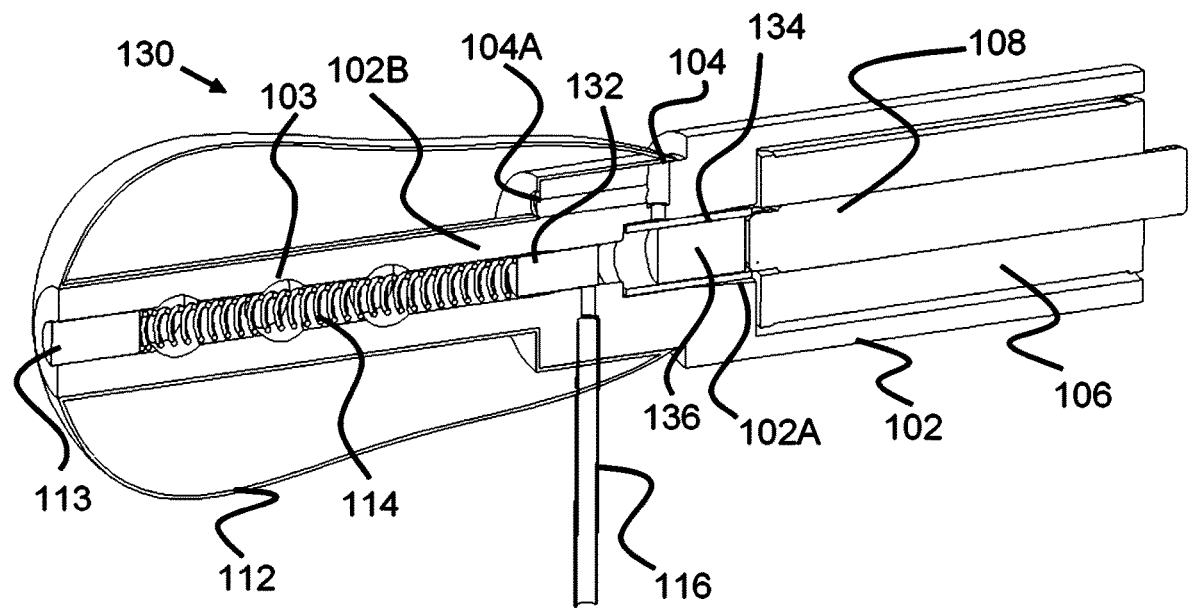
Figure 9B:
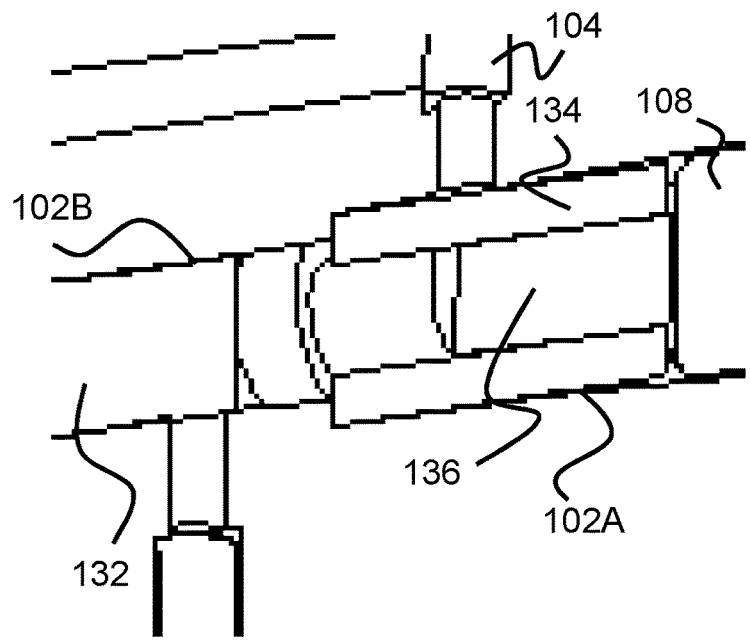

In FIGS. 9A and 9B, the power to the solenoid 106 is turned off so that the plunger 108 no longer applies leftward pressure. With reduced fluid in the pump chambers and a lack of force from the plunger 108, the compressed spring 114 pushes the delivery piston 132 rightward, thereby blocking off the delivery port 116.

Figure 10A:
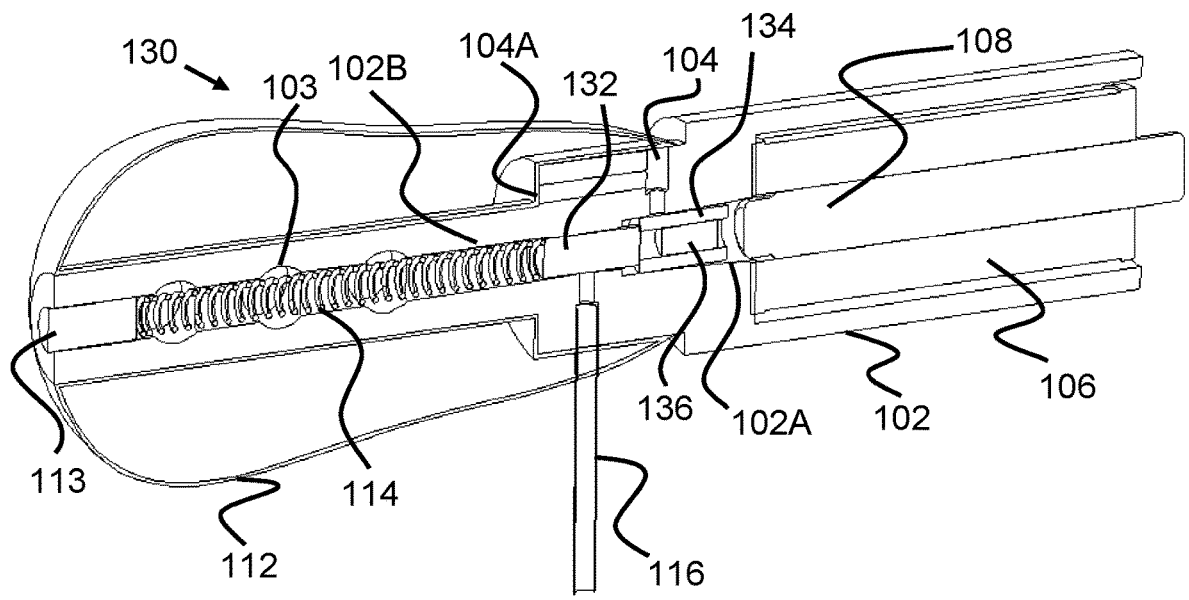
Figure 10B:
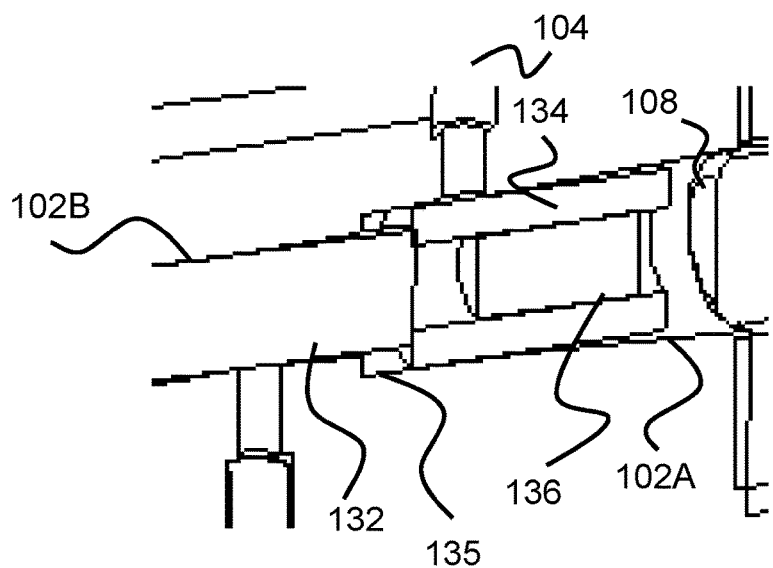

In FIGS. 10A and 10B, the delivery piston 132 continues to move to the right, contacting and pushing the fill piston 134. As seen best in FIG. 10B, the delivery piston 132 and fill piston 134 stop their movement as a hydraulic lock point is created by the chamber formed at location 135. This hydraulic lock point is eliminated as fluid from within the chamber within the fill piston 134 migrates into area 135

Figure 11A:
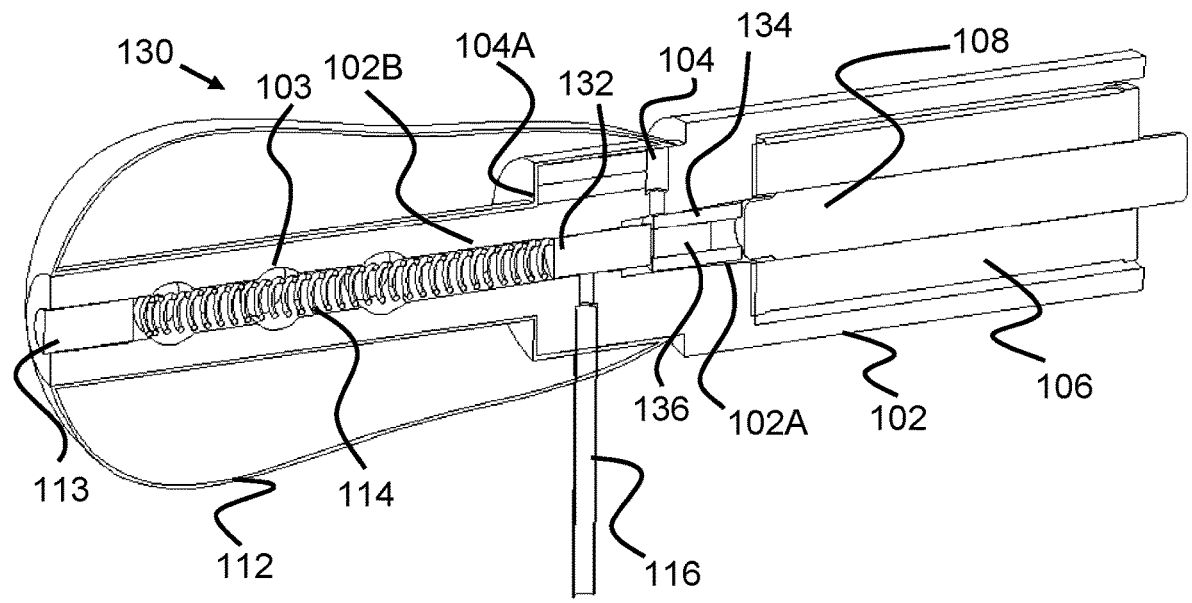
Figure 11B:
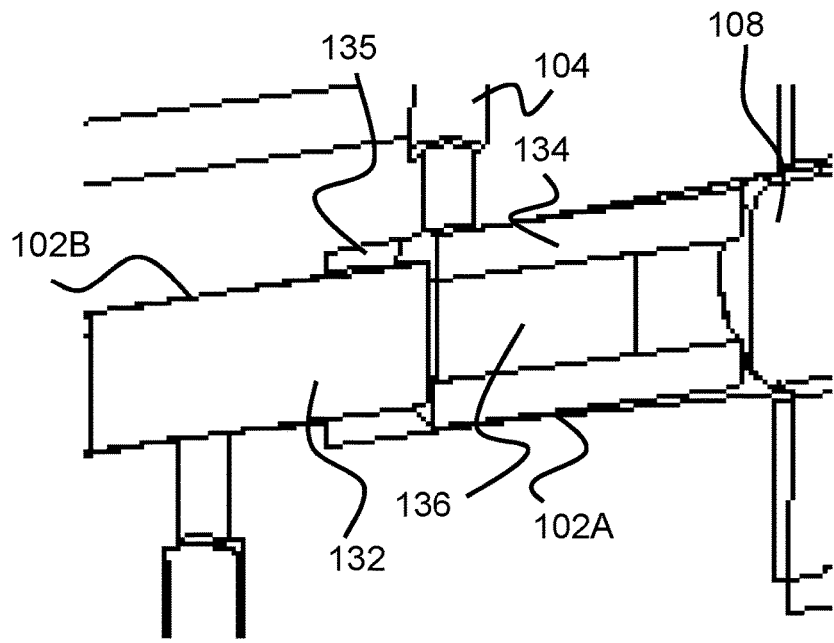

(e.g., via a small gap formed between the right side of the delivery piston 132 and the left side of the fill piston 132). As the fluid moves to area 135, the refill piston 136 moves further to the left while the delivery piston 132 and fill piston 134 move to the right, as seen in FIGS. 11A and 11B. Eventually, the fill piston 134 moves far enough to the right to open the input passage 104 and the pump cycle can begin again.

FIGS. 12-16 illustrate another embodiment of a pump 140 according to the present invention. The pump 140 is generally similar to the previously described pumps 100 and 130. However, the pump 140 includes an elastomeric fill sleeve 144 disposed around the fill piston 142, selectively opening and closing the input passage 104 during operation.

Figure 12A:
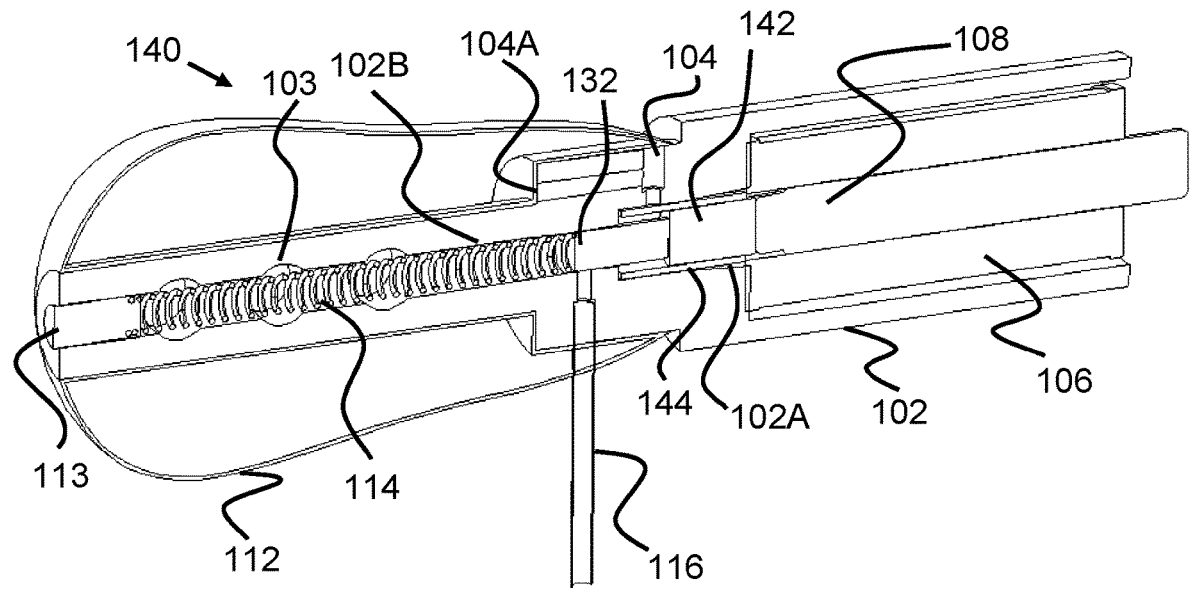
FIGS. 12A-16B illustrate another embodiment of a fluid pump according to the present invention.
Figure 12B:
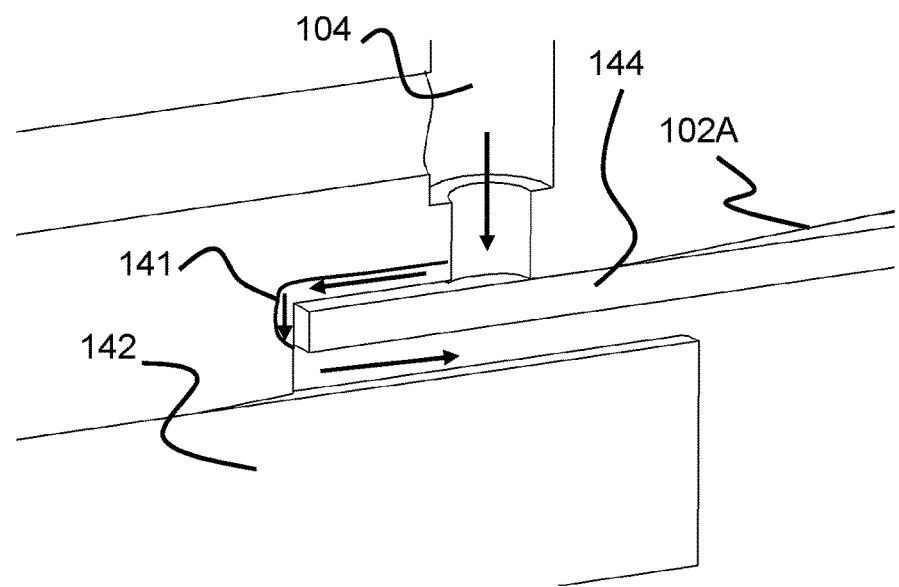

In FIG. 12A, the solenoid 106 remains unactuated (i.e., no power is applied) and the plunger 108 is fully retracted to the right. The delivery piston 132 is positioned to block the output port 116 and the fill piston is positioned against the plunger 108 and the delivery piston 132. As described below, during a normal cycle, hydraulic lock pressure is created in the chamber formed between the delivery piston 132 and the elastomeric fill sleeve 144. This force pulls the elastomeric sleeve 144 away from a bypass channel 141 (seen in FIG. 12B) that connects between the input passage 104 and the larger diameter chamber 102A, thereby opening the input passage 104 and allowing fluid to be sucked into the pump 140.

Figure 13A:
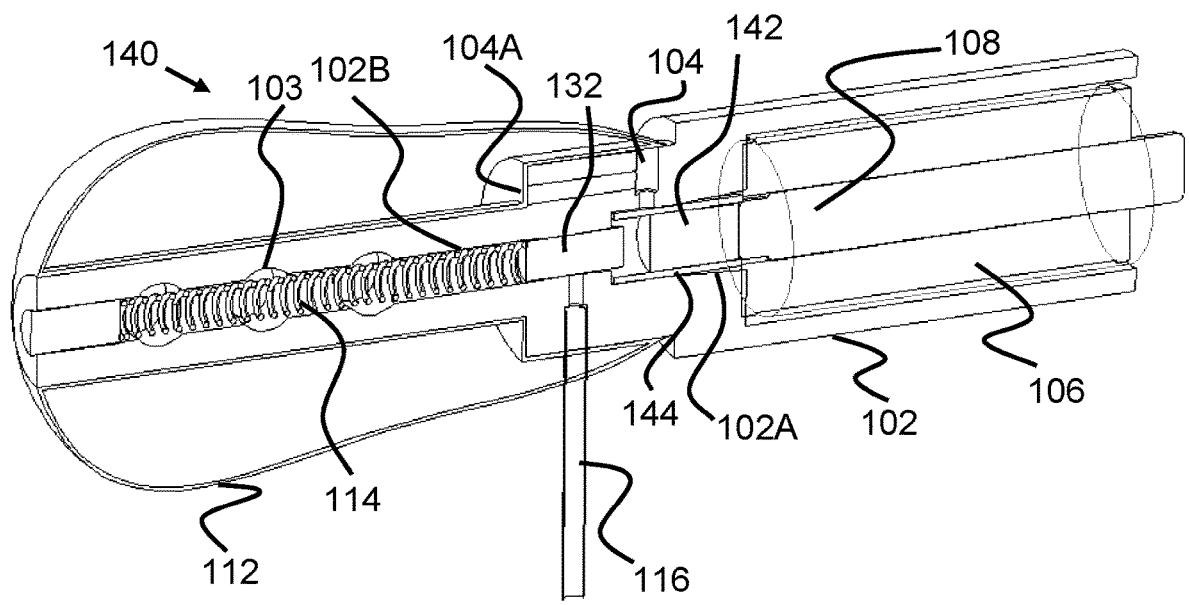
Figure 13B:
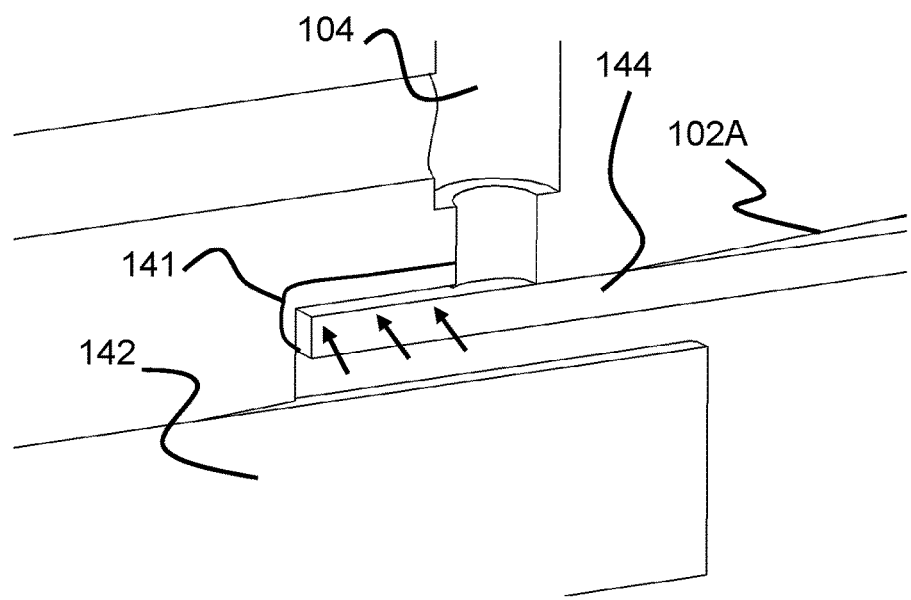

In FIG. 13A, fluid has entered the chamber 102A. As the solenoid 106 is actuated, the plunger begins to exert pressure on the fill piston 142 and thereby create pressure within the chamber 102A. As seen in FIG. 13B, this pressure pushes the elastomeric sleeve upwards into the bypass channel 141, filling the channel 141 and closing of the input passage 104.

Figure 14:
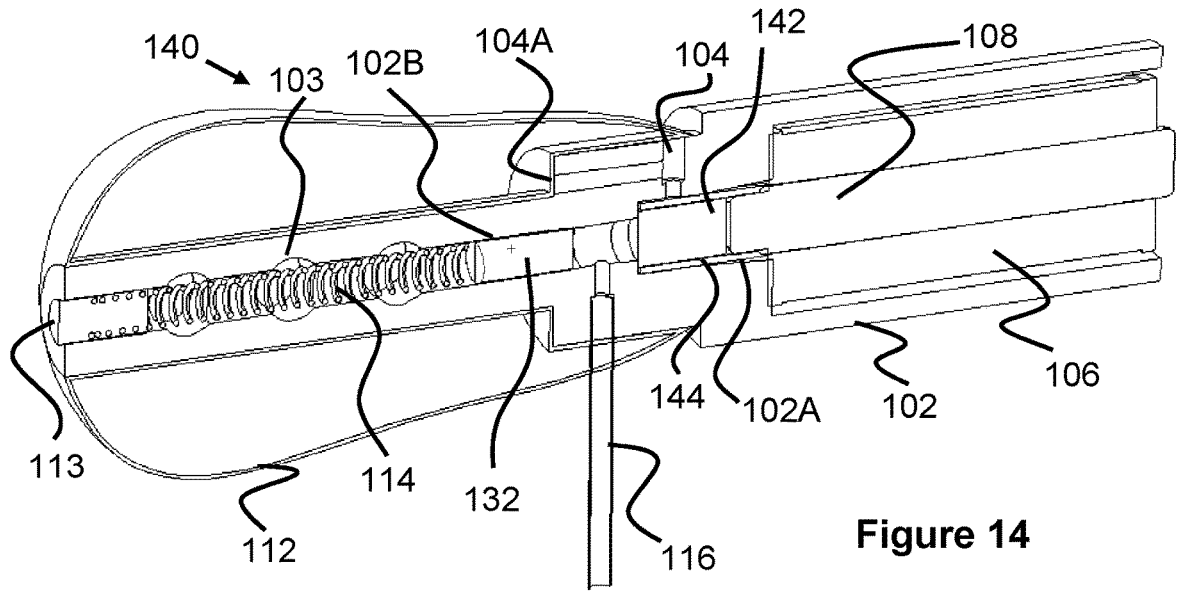

In FIG. 14, the plunger 108 moves further to the left, increasing pressure within the chambers 102A and 102B. This increased pressure causes the delivery piston 132 to slide to the left, past the output port 116, causing a portion of the fluid in the pump 140 to be expelled.

Figure 15:
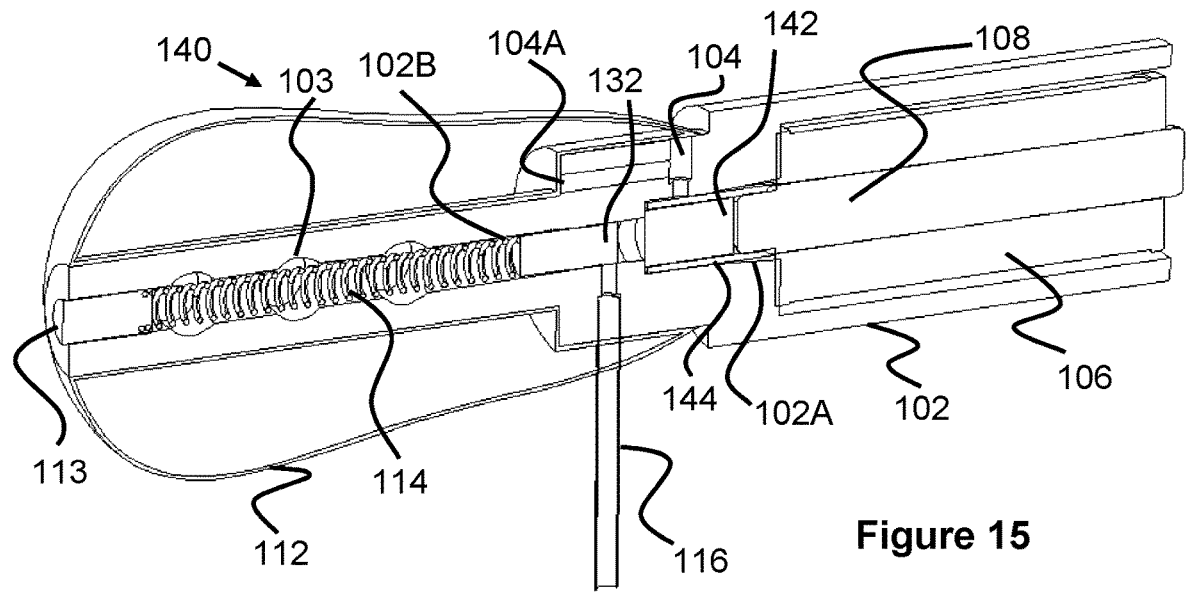

As the fluid leaves the chamber 102B, the pressure in the chamber 102B reduces. Additionally, the power to the solenoid 106 is deactivated, allowing the compressed spring 114 to push the delivery piston 132 back to the right, closing the output port 116 as seen in FIG. 15.

Figure 16A:
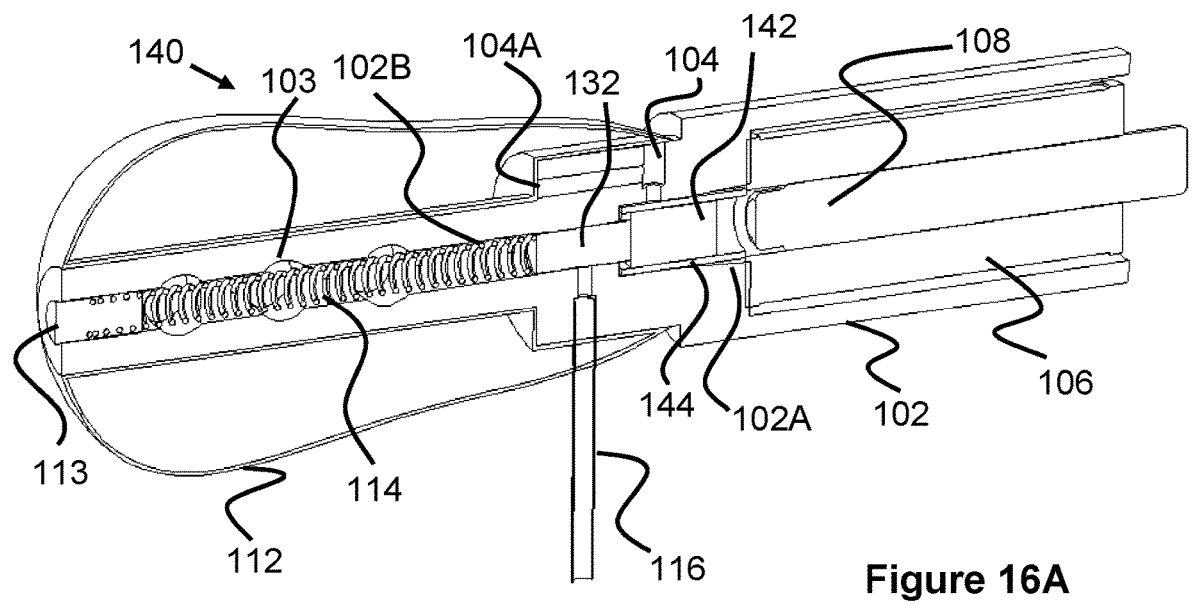
Figure 16B:
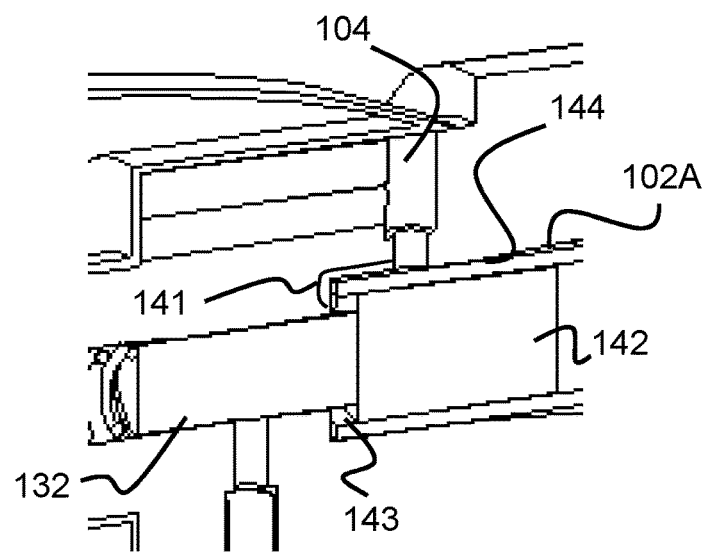

As seen in FIGS. 16A and 16B, as the delivery piston 132 continues to move to the right, an area 143 is created between the delivery piston 132 and the elastomeric sleeve 144, creating a hydraulic lock. The force of the hydraulic lock pulls downward on the elastomeric sleeve 144, away from the channel 141, pulling additional fluid into the chamber 102A. This ultimately results in the configuration seen in 13A and allows the pump cycle to be repeated.

Pump Enclosure with Multiple Chambers

In another embodiment according to the present invention, FIGS. 17-26 illustrate various aspects of a pump enclosure 150 having multiple chambers to accommodate multiple pumps. While this embodiment of the pump enclosure 150 accommodates up to 4 fluid pumps, it should be understood that the enclosure could also be configured for different numbers of pumps, such as 2, 3, 5, and 6. Any of the pumps previously described in this specification (or variations thereof) lend themselves particularly well to use in the present pump enclosure 150, due to the relatively small size of the pumps and the relatively low power consumption afforded by the solenoid 106 (or similar actuator mechanism).

Figure 17:
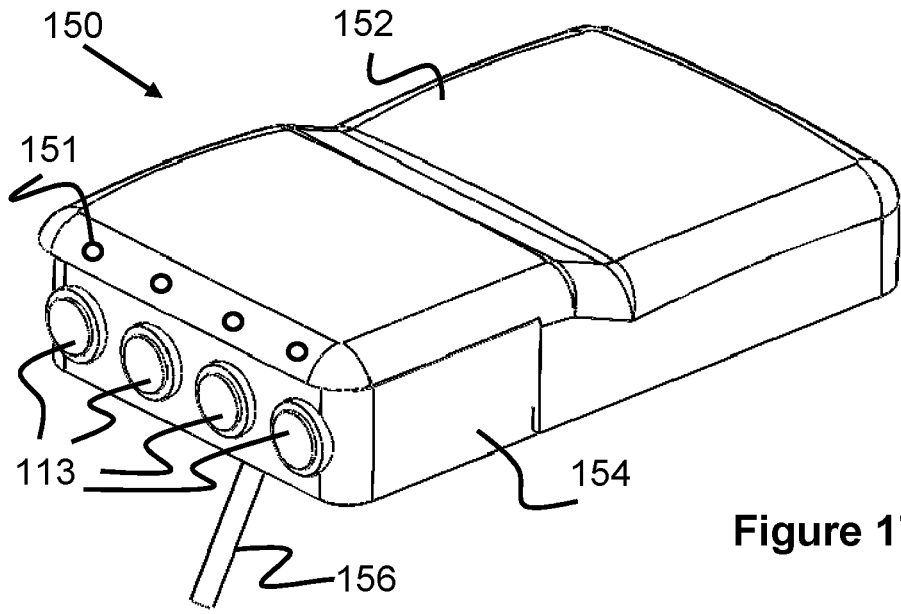
FIGS. 17-26 illustrate an embodiment of a pump enclosure having multiple fluid chambers and pumps.
Figure 18:
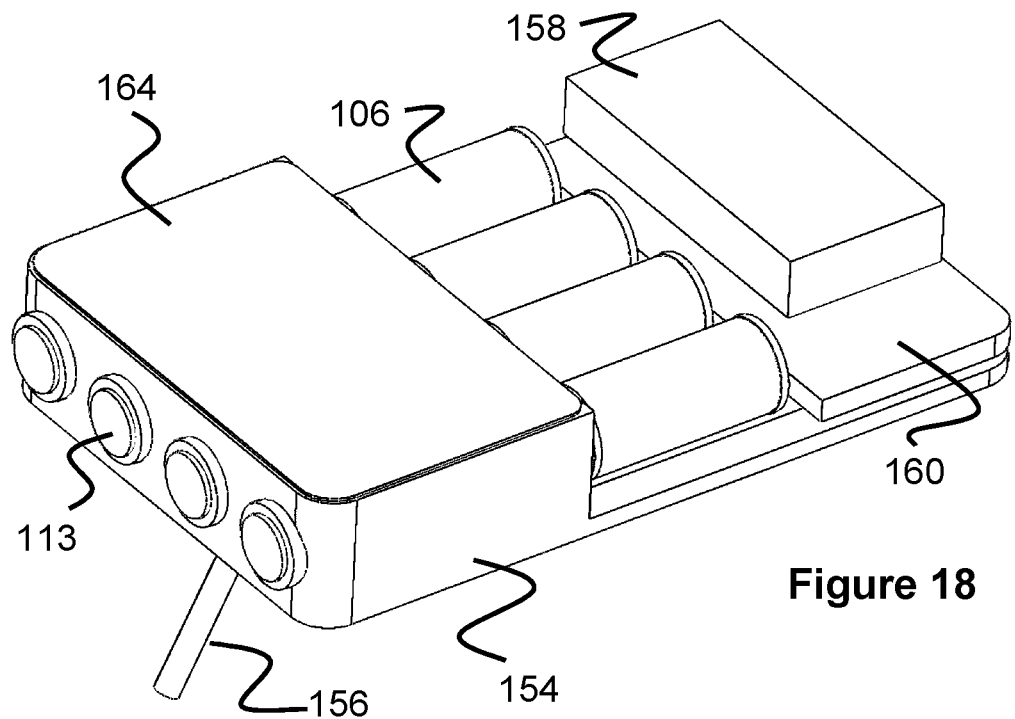

FIG. 17 illustrates the pump enclosure 150, having a lower housing member 154, an upper housing cover 152, a cannula 156 (or rigid needle), and a plurality of septums 113 from each of the pumps within the enclosure 150. FIG. 18 illustrates the enclosure 150 with the upper housing cover 152 removed, exposing a top sealing cover or film 164, a plurality of solenoids 106 that drive each of the pumps, a battery 158, and a circuit assembly 160 comprising a plurality of electrical components that control and operate the enclosure 150.

Figure 19:
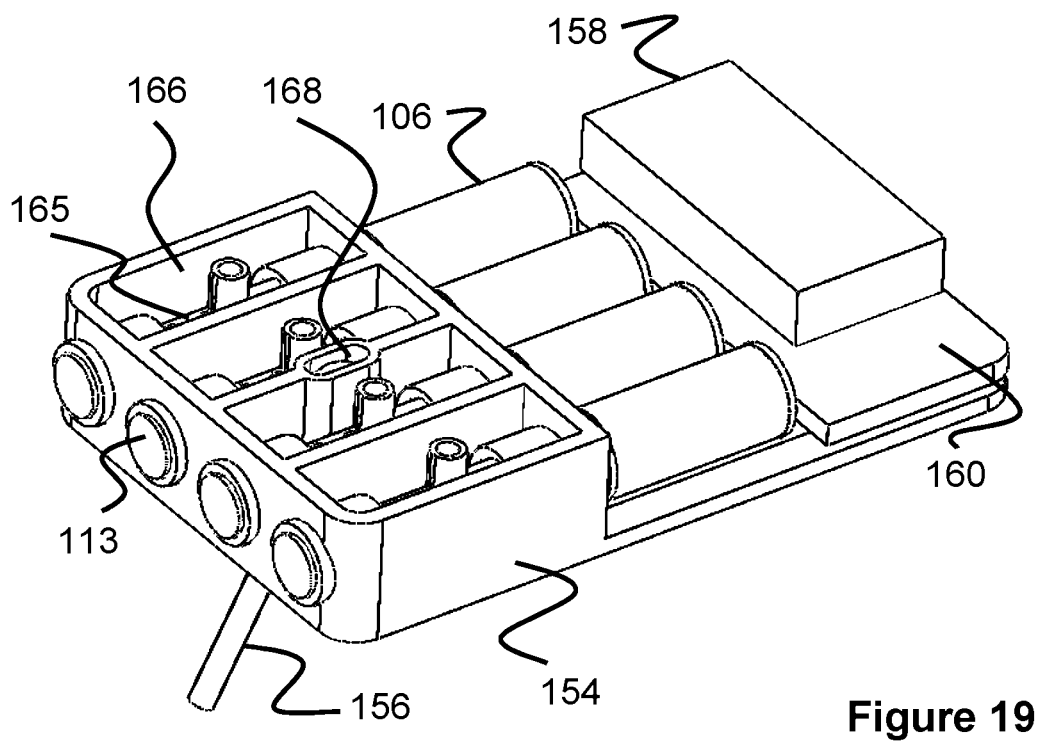
Figure 20:
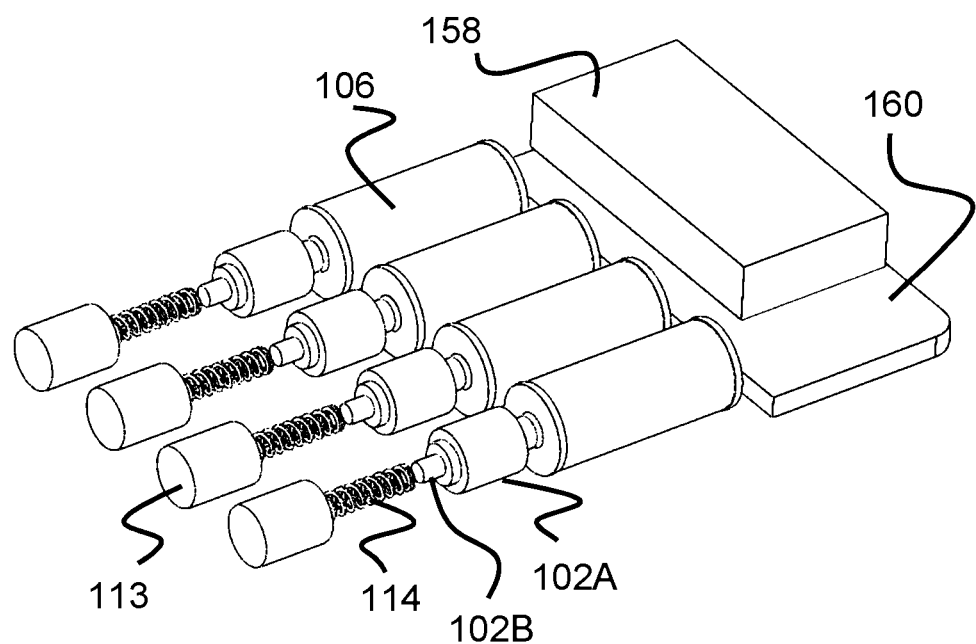
Figure 21:
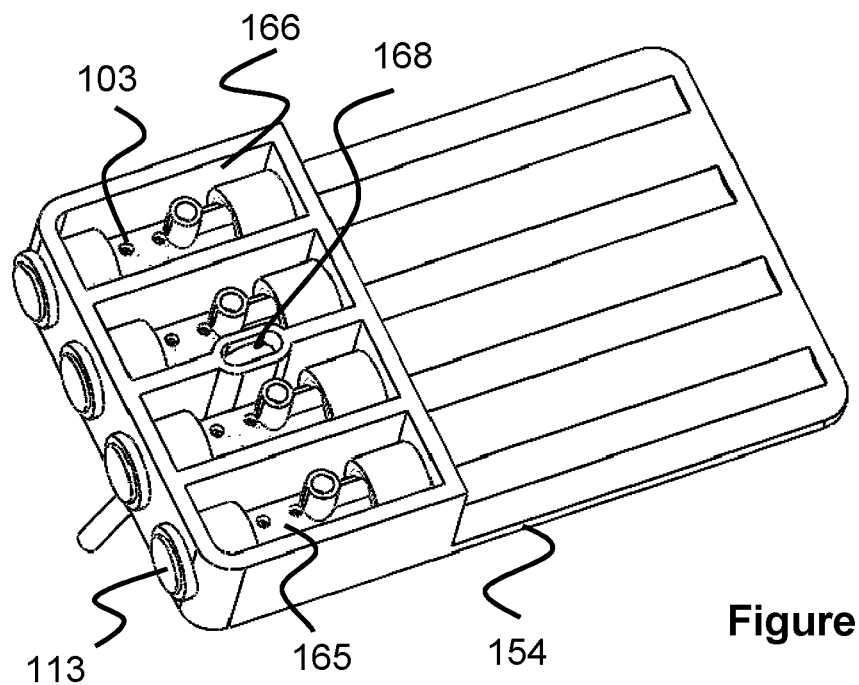

FIG. 19 illustrates a similar view of the enclosure 150 as the prior figure, except that the film 164 has been removed to expose four pump chambers 166. Each chamber 166 includes pump housings 165 (also seen in FIG. 21) that are similarly shaped to those of the pump housing 102, as described in previously described pump embodiments. In this regard, the pump components shown in FIG. 20 (e.g., the septum 113, spring 114, and chambers 102A, 102B) are located within passage created within each housing 165.

In one embodiment, the walls of the chambers 166 and the film 164 create the fluid chamber (e.g., fluid chamber 112). Alternately, a flexible bag or container can be located within the each chamber 166 to act as the fluid chamber.

Figure 22:
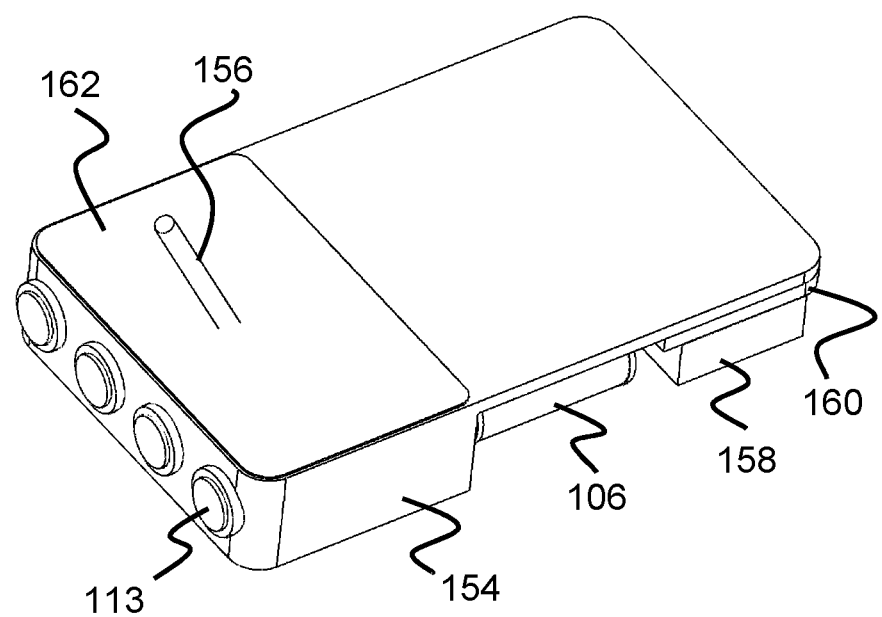
Figure 23:
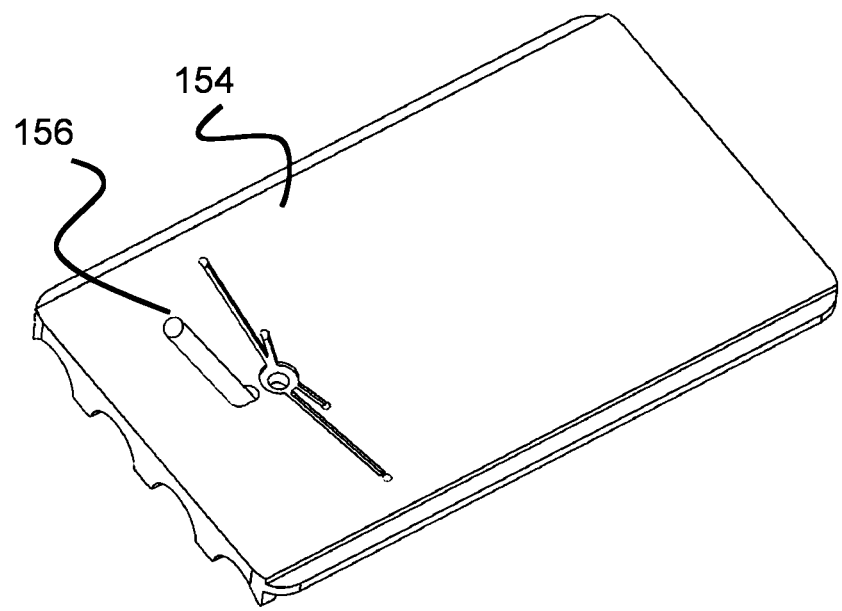
Figure 24:
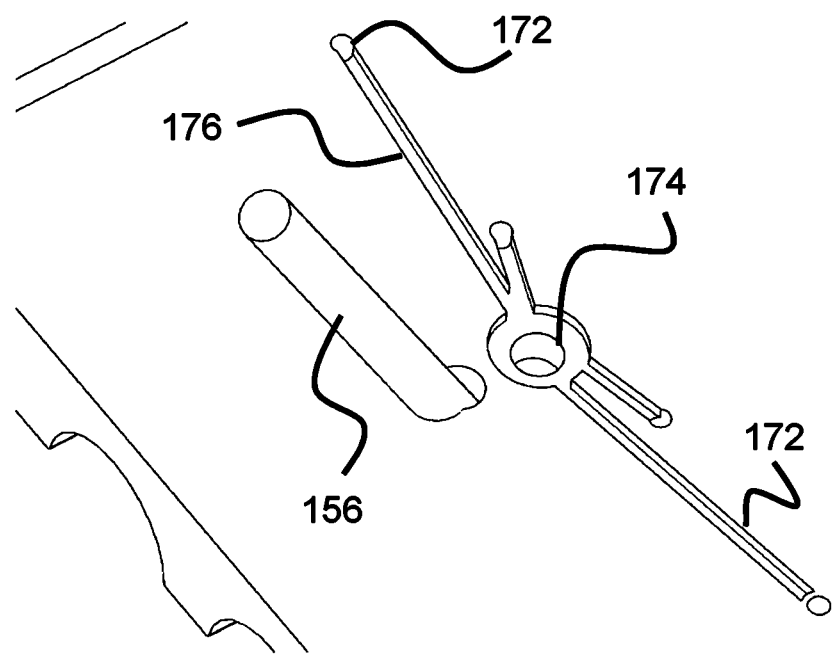
Figure 25:
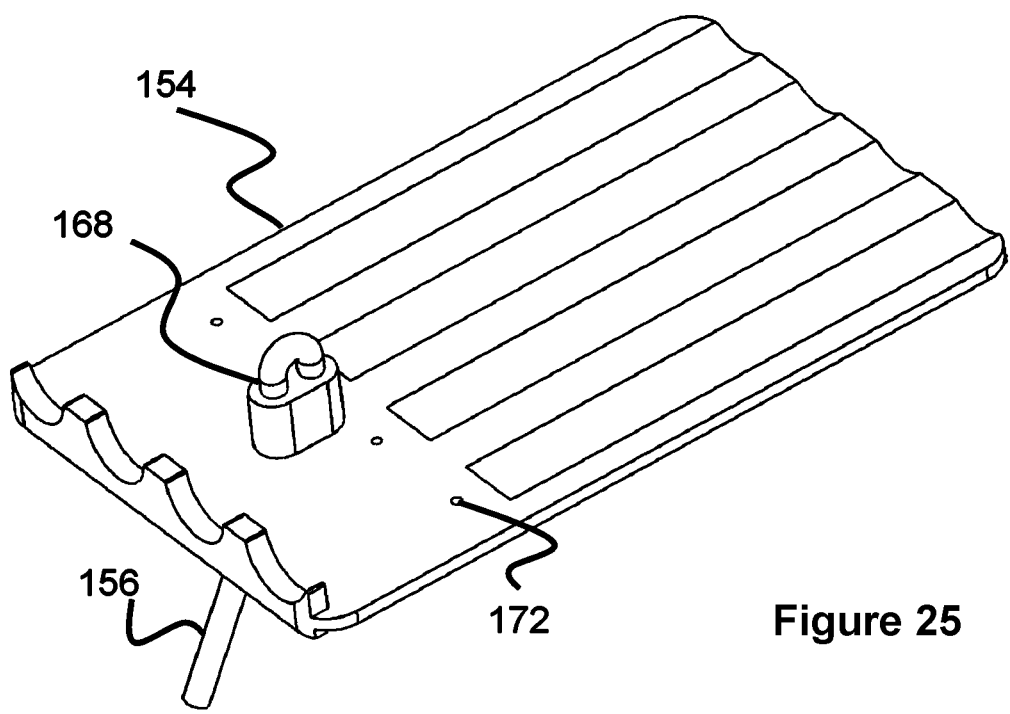
Figure 26:
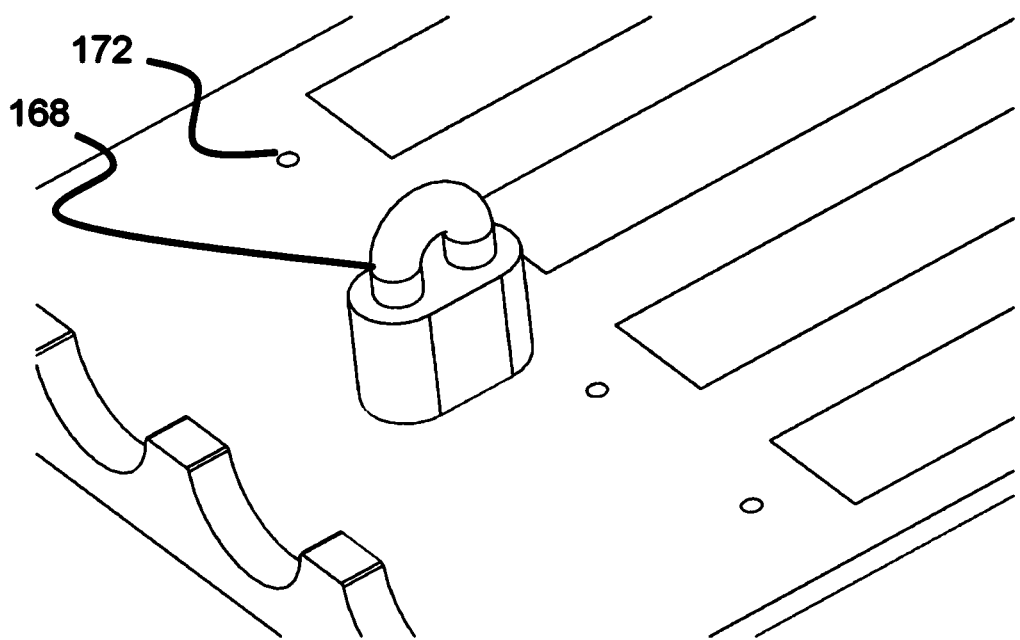

The output ports 116 of each of the pumps are connected to apertures 172 in the lower housing member 154, as seen best in FIGS. 23-25. These apertures 172 each connect to a channel 176 on the lower side of the housing member 154 that connects to a single aperture 174. These channels 176 can be formed into a sealed passage system with a lower plate or film 162 fixed over both the channels 176 and the aperture 174, as seen in FIG. 22. As best seen in FIGS. 25 and 26, the aperture 177 connects with a curved septum passage 168, which allows the cannula 156 (or rigid needle) to connect with the pump enclosure and receive the fluid from any/all of the pumps.

In an alternate embodiment, the output port of one or more of the pumps can be directly connected to a fluid chamber of an adjacent pump, allowing the contents of one fluid chamber to be delivered to the fluid chamber of another pump.

It should be understood that the circuit assembly 160 includes a variety of circuitry to operate the pumps of the controller, as well as any other electrical components that may be present. For example, the circuit assembly 160 may include a microprocessor or microcontroller, a memory, software stored in the memory and executed by the microprocessor/microcontroller, sensors (e.g., pressure sensor, temperature sensor), and a communications port.

It should be understood that a variety of different drugs and combinations of drugs are possible for each of the fluid chambers of the pump enclosure 150. Several enclosure examples and methods of use are discussed below, however, each of these drugs can be mixed and matched in many different configurations, all of which are contemplated in the present invention.

Figure 26A:
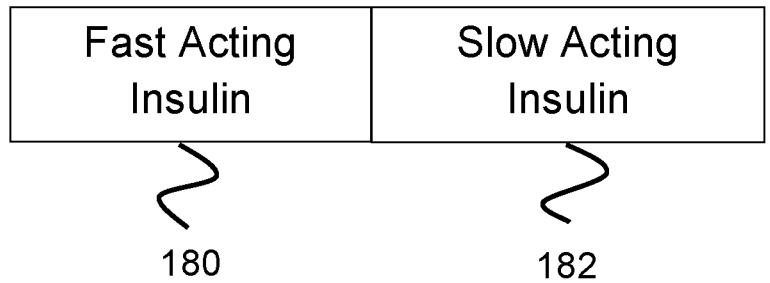
Figure 27:
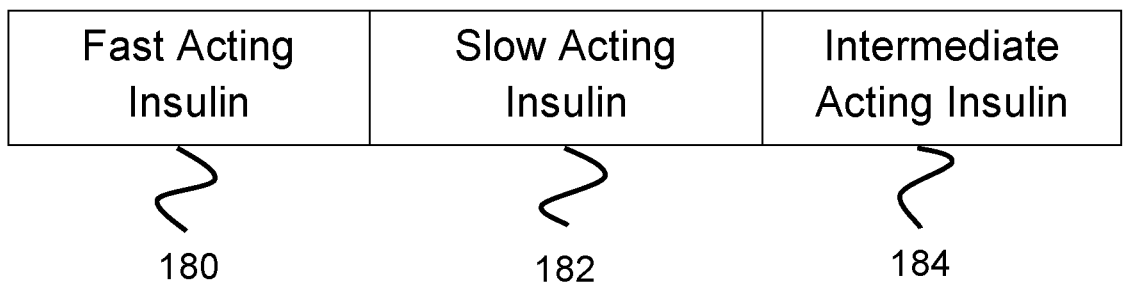

In one embodiment, multiple fluid chambers may have two or more types of insulin with different pharma kinetic actions. In one example seen in FIG. 26A, at least one fluid chamber of the enclosure may contain a fast acting insulin 180, such as lispro, aspart, and glulisine, and another chamber may contain a slow acting insulin 182, such as insulin glargine or insulin detemir. In another example seen in FIG. 27, an intermediate acting insulin may also be included in another chamber of the enclosure 150, such as NPH.

Emergency rescue pens are used by diabetics when their glucose goes low and they begin to show signs of hypoglycemia. These pens combine liquid and lyophilized powder to form a glucagon fluid that is stable for about 24 hours. Typically, all of the fluid is immediately used.

Figure 28:
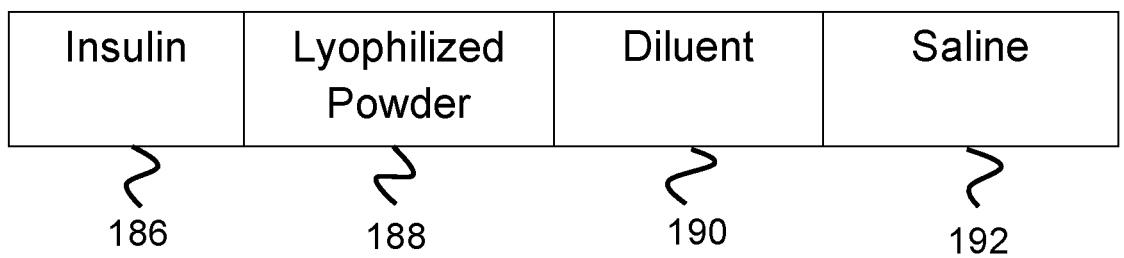

Another configuration of the enclosure 150 can combine the functionality of such an emergency rescue pens with typical insulin pump functionality. For example, FIG. 28 illustrates a first chamber containing insulin 186 for normal insulin pump operation, a lyophilized powder 188 in a second chamber, a diluent 190 in a third chamber, and saline 192 in a fourth chamber. The output port of the third pump can be configured to lead only to the second chamber, allowing the third chamber's pump to move into the second chamber with the lyophilized powder to create glucagon. The second chamber's pump can then be activated to output glucagon to the patient. Finally, the saline 192 of the fourth chamber can be used to rinse the cannula/needle of any glucagon residue.

Figure 29:
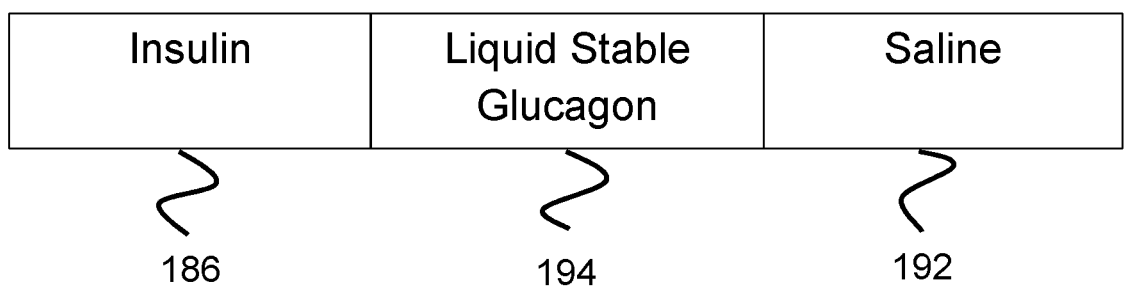

FIG. 29 illustrates a similar example to that of FIG. 28, except that instead of mixing both a powder and diluent, a liquid stable glucagon is used in a second chamber.

Figure 30:
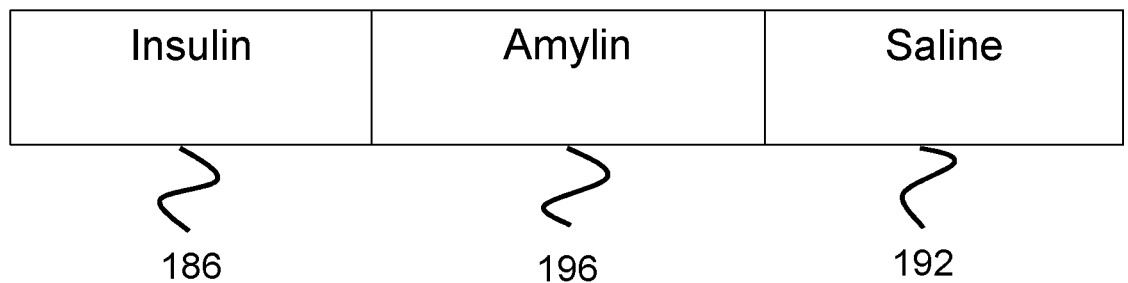

FIG. 30 illustrates another configuration of the enclosure 150 in which amylin 196 is included in one of the chambers to slow post prandial emptying to better regulate the speed of insulin activation and thereby better match glucose uptake.

As mentioned above, a pump enclosure may include one or more, or even all of the following in different fluid chambers of the enclosure: Fast acting insulin, slow acting insulin, intermediate acting insulin, lyophilized powder, diluent, saline, liquid stable glucagon, and/or amylin. Again, the saline can be used to flush the channels of the enclosure and the cannula/needle to remove any residual drugs and prevent an inadvertent mixing during delivery.

In another embodiment of the present invention, one of the pumps of the pump enclosure 150 can be configured for measuring glucose. Specifically, one pump is configured to move fluid from the cannula 156 to a testing chamber in the pump. Unlike traditional CGMS needles that require a separate stick, by waiting between interstitial drug dosages, the interstitial fluid washes through the drug. During this time, a small amount of fluid inside the cannula and outside the cannula could be drawn in to test the level of glucose at the site and correlate it back to a blood plasma glucose level. Furthermore, the cannula could have the glucose oxidase inside of it with electrodes to measure within the cannula.

In another aspect of the present invention, the enclosure 150 includes a plurality of indicators 151, such as LED lights, that correspond to and are located near a specific pump and septum 113 within the enclosure 150. In this respect, activation of the indicator 151 may be used to indicate a status of a pump. For example, the indicator 151 may indicate that a fluid reservoir is empty or that a pump has become broken. The indicator 151 may be capable of illuminating a single color or multiple colors, each of which indicate a different status (e.g., green means operational, yellow means empty fluid reservoir, and red means a broken pump).

In another aspect of the present invention, the enclosure may include a single indicator 151 that illuminates in several different colors that each correspond to a color of a septum 113. For example, the first septum 113 may be green and the second may be blue. When the indicator 151 illuminates in either of these colors, the user is made aware that the fluid reservoir for that pump is empty and therefore requires filling. Alternately, each septum 113 could have a different shape (e.g., circle, square, triangle), number, or other indicator, and a display on the enclosure may also display these indicators as necessary to indicate empty fluid reservoirs.

Pump Feedback

One further benefit of the pump embodiments and pump enclosure embodiments of the present invention is that they can allow various aspects of pump cycles to be measured, so as to allow onboard circuitry to determine if the pump mechanism is operating properly. For example, with certain measurements, pump enclosure circuitry may determine if the pump mechanism is delivering the proper or expected quantity of fluid.

Figure 31:
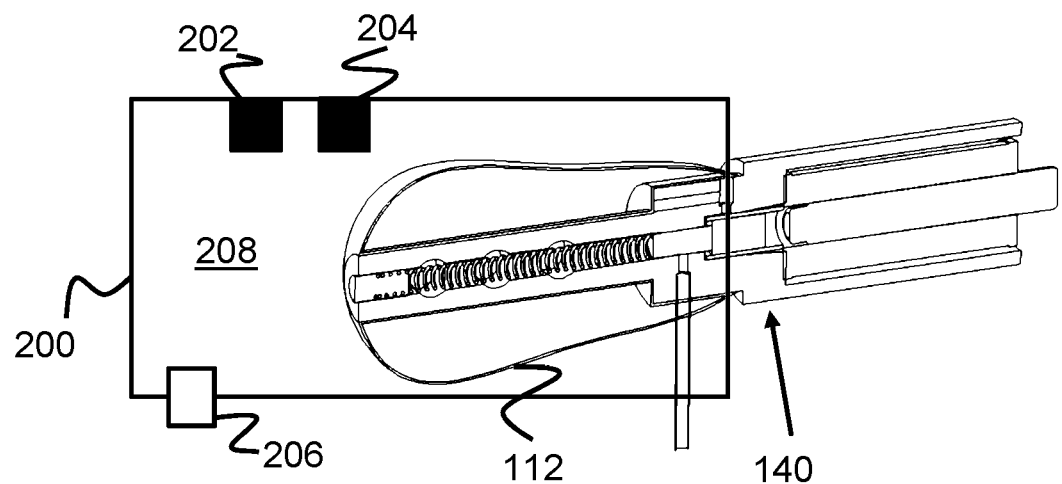
FIG. 31 illustrates a feedback system for a pump enclosure.
Figure 32:
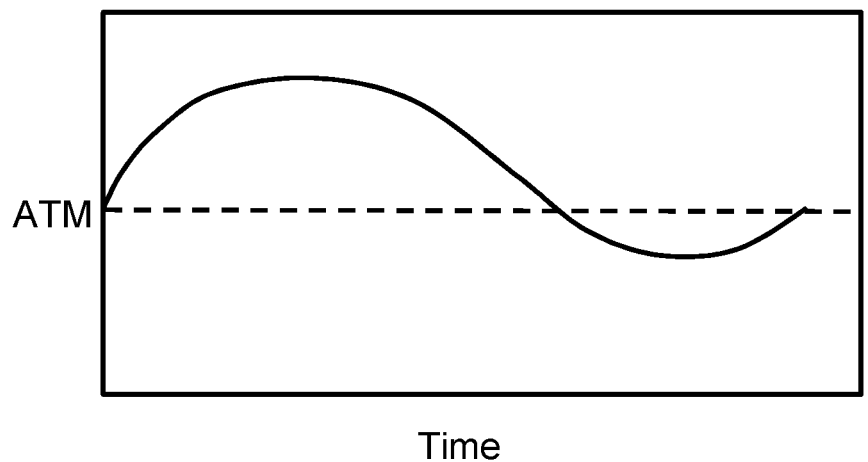
FIG. 32 illustrates an example pressure measurement from the feedback system in FIG. 31.

FIG. 31 illustrates an embodiment of a pump enclosure 200 having a pressure sensor 202, a temperature sensor 204, and a gas restrictor 206, all of which are either located in or are in communication with a gas or air chamber 208. As the pump 140 operates, it increases and decreases the amount of fluid in its flexible fluid chamber 112. For example, the pump 140 may initially increase the amount of fluid in the fluid chamber 112 during its filling portion of its cycle and then decrease the amount of fluid during delivery of the fluid to the patient. These increases and decreases in volume of the fluid within the air chamber 208 of the enclosure 200 increase or decrease the air pressure within the air chamber 208 (e.g., as seen in FIG. 32).

By measuring the pressure and temperature of the air/gas within the air chamber 208, the enclosure's onboard circuitry can determine the volume of the air chamber 208 that is not occupied by the fluid chamber 112 with Boyle's Law. This volume can be subtracted from the known volume of the air chamber 208 with an empty fluid chamber 112 to determine the fluid volume.

If the air chamber 208 was completely sealed, a vacuum could be created within the chamber 208 as fluid is pumped out of the fluid chamber 112. Since such a vacuum could ultimately hinder operation of the pump 140, an air restrictor 206 can be used to slowly vent and thereby slowly equalize the air chamber 208 with the atmosphere. The previously described fluid volume calculations can still be performed by also compensating for the resistance to airflow through the restrictor 206 using Poiseuille's Law. Poiseuille's Law of fluid flow determines the amount of fluid that passes through a restriction as a function of the viscosity, pressure differences, size of the restriction and length. By adding a restriction of known physical characteristics and measuring the pressure on one side (and knowing the pressure on the other side by measuring it during static conditions), the changes in the gas and liquid volume can be measured and determined dynamically.

These measurements and calculations by the onboard circuitry/software could identify how quickly the actuator (e.g., solenoid 106) is moving the pump elements, how far the delivery piston has moved due to the displacement of fluid, how much fluid has returned to the fluid chamber when the motion begins at the neutral position and the rate of flow from the delivery chamber to the output. This occurs because there are two functions at work, the displacement of fluid out of the delivery chamber and the flow of gas through the restriction due to the pressure differentials.

Figure 33:
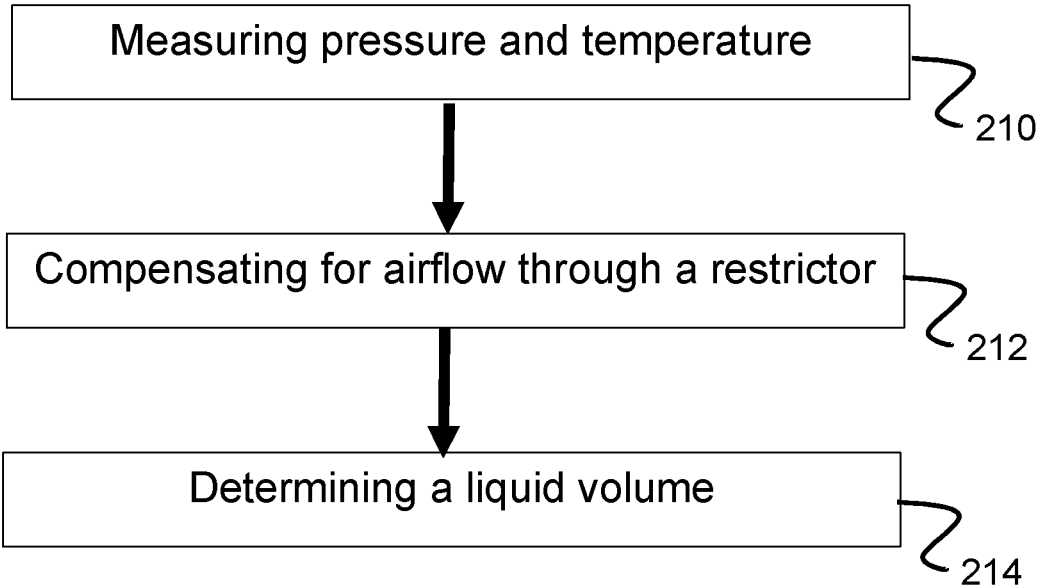
FIG. 33 illustrates a flow chart of a method for determining a liquid volume via the feedback system of FIG. 31.

In this respect, the present invention contemplates a method of a pump enclosure measuring pressure and temperature within an air chamber 208 (step 210), compensating for airflow through a restrictor 206 connected to the air chamber 208 (step 212), and determining a volume of fluid in a fluid chamber 112 (step 214), as seen in FIG. 33.

The restrictor 206 can be made of rigid materials, such as, rubies, diamonds, glass, plastic, and other materials commonly used in the practice. The flow characteristics of the restrictor 206 can be characterized or calibrated during the initial pumps (by the onboard circuitry/software) when the volume in the fluid chamber 112 is known and the air chamber 208 is known. The enclosure may also be calibrated by performing volume calculations via the circuitry/software, injecting a known volume of liquid into the fluid chamber 206, inputting the volume into an interface associated with the enclosure, performing a second volume measurement, and then comparing the difference between the injected amount and the calculated amount. In the case of either method, the changes in pressure can be used to determine the resistance caused by the restrictor 206, accounting for variations in manufacturing and dirt or other changes that may change the behavior of the restrictor 206 over time.

Preferably, the restrictor 206 is sized small enough such that the small pressure created in the movements internally are insufficient to pull liquid into the air chamber 208, due to the surface tension characteristics of the restrictor 206. This may prevent water and other fluids from being sucked into the air chamber 208 during cleaning, showers, and swimming, for example.

Figure 34:
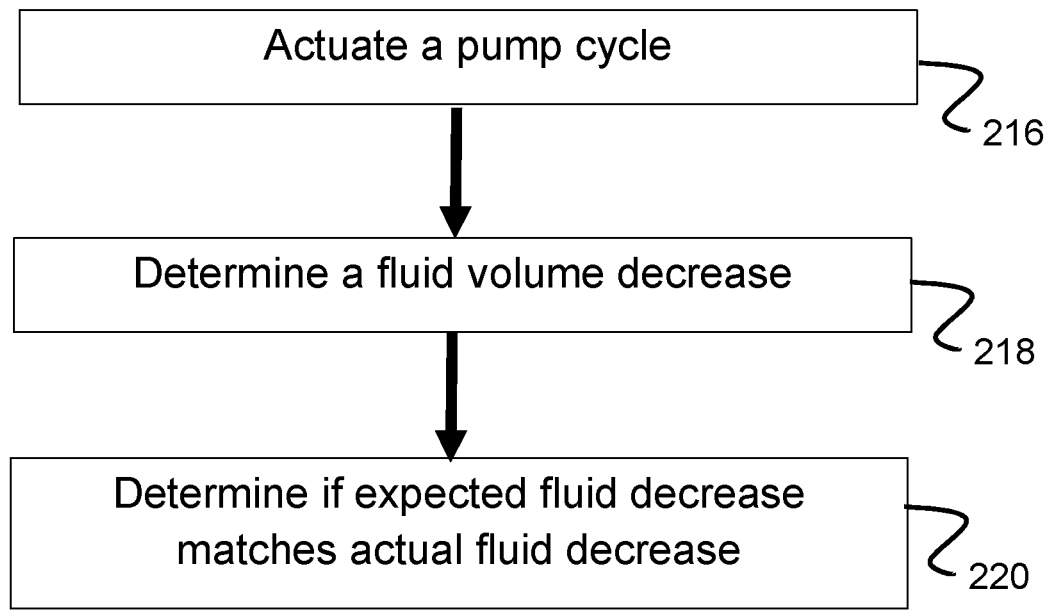
FIG. 34 illustrates a method of determining if a fluid pump is pumping an expected amount of fluid.

It should be understood that by monitoring fluid volume in the fluid chamber 112, a variety of different diagnostics and alerts are possible. For example, FIG. 34 illustrates a method of determining if a fluid pump is pumping an expected amount of fluid. First, a pump cycle is actuated as explained with regard to several of the different pump embodiments of the present specification (step 216). Next, the electronics and software of the pump enclosure 200 compare a calculated fluid volume of the fluid chamber 112 from before the previous pump cycle to a calculated fluid volume after the pump cycle (step 218). Finally, the electronics and software of the pump enclosure 200 determine if the expected fluid decrease matches the measured fluid decrease (step 220). If the two fluid volume decreased do not "match" (e.g., are not within 5% of each other), the electronics and software of the pump enclosure 200 may generate a warning (e.g., on an interface on the pump enclosure or a separate interface connected to the pump enclosure via a wired or wireless communications protocol).

While pressure measurement can be used to monitor pumping cycles, the pumping cycles could also be monitored by including a cycle counting sensor. For example, a Reid or Hall effect sensor could be used to monitor movement of various pistons in the pump. In this respect, the pump enclosure's electronics and software could alert the user when an expected pump fails to occur or when a greater number of pump cycles occur than expected.

In one aspect of the present invention, the pump enclosure 200 may include a multicolor light (e.g. a tricolor LED) that indicates the cycle of a pump within the pump enclosure. For example, a yellow light may indicate a pressure increases to an acceptable level, a green light may indicate that the pressure has dissipated due to deliver of the fluid, and a red light may indicate that an unexpected sensor/pressure/volume value.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An insulin pump enclosure, comprising:
   a housing having an outlet;
   a first pump located within said housing and being connected to output fluid to said outlet, said first pump comprising:
   a first pump chamber including a first large diameter pump chamber and a first small diameter pump chamber,
   a first input port in communication with the first large diameter pump chamber,
   a first output port in communication with the first small diameter pump chamber and the outlet,
   a first delivery piston which moves within the first large diameter pump chamber and the first small diameter pump chamber, which is coupled to a first spring and which blocks the first output port when the first pump is in a neutral position, and
   a first displacement mechanism including a fast action on/off cycle and a plunger that translates after pulsed actuation of the first displacement mechanism so as to increase pressure within the first pump chamber and translate the first delivery piston between the first large diameter pump chamber and the first small diameter pump chamber; and
   a second pump located within said housing and being connected to output fluid to said outlet, said second pump comprising:
   a second pump chamber including a second large diameter pump chamber and a second small diameter pump chamber,
   a second input port in communication with the second large diameter pump chamber,
   a second output port in communication with the second small diameter pump chamber and the outlet,
   a second delivery piston which moves within the second large diameter pump chamber and the second small diameter pump chamber, which is coupled to a second spring and which blocks the second output port when the second pump is in a neutral position, and
   a second displacement mechanism including a fast action on/off cycle and a plunger that translates after pulsed actuation of the second displacement mechanism so as to increase pressure within the second pump chamber and translate the second delivery piston between the second large diameter pump chamber and the second small diameter pump chamber.

2. The insulin pump enclosure of claim 1, further comprising a third pump located within said housing and being connected to output fluid to said outlet, and a fourth pump located within said housing and being connected to output fluid to said outlet.

3. The insulin pump enclosure of claim 2,
   wherein the third pump located within said housing is connected to output fluid to a second fluid reservoir, and the fourth pump located within said housing is connected to output fluid to said outlet; and
   wherein said first pump is connected to a first fluid reservoir containing insulin, said second pump is connected to said second fluid reservoir containing lyophilized powder, said third pump is connected to a third fluid reservoir containing diluent, and said fourth pump is connected to a fourth fluid reservoir containing saline; wherein said third pump is configured to deliver said diluent to said second fluid reservoir so as to create glucagon.

4. The insulin pump enclosure of claim 1, wherein said first pump is connected to a first fluid reservoir containing fast acting insulin and said second pump is connected to a second fluid reservoir containing slow acting insulin.

5. The insulin pump enclosure of claim 1, further comprising a third pump located within said housing and being connected to output fluid to said outlet, wherein said first pump is connected to a first fluid reservoir containing insulin, said second pump is connected to a second fluid reservoir containing amylin, and said third pump is connected to a third fluid reservoir containing saline.

6. The insulin pump enclosure of claim 1, further comprising a third pump located within said housing and being connected to output fluid to said outlet, wherein said first pump is connected to a first fluid reservoir containing insulin, said second pump is connected to a second fluid reservoir containing liquid stable glucagon, and said third pump is connected to a third fluid reservoir containing saline.

7. The insulin pump enclosure of claim 1 wherein the first displacement mechanism comprises a solenoid and the second displacement mechanism comprises a solenoid.

8. An insulin pump enclosure, comprising:
a housing having an outlet;
a pump located within said housing and being connected to output fluid to said outlet, said pump comprising:
  a pump chamber including a large diameter pump chamber and a small diameter pump chamber,
  an input port in communication with the large diameter pump chamber,
  a first output port in communication with the small diameter pump chamber and the outlet,
  a delivery piston which moves within the large diameter pump chamber and the small diameter pump chamber, which is coupled to a spring and which blocks the output port when the pump is in a neutral position, and
  a displacement mechanism including a fast action on/off cycle and a plunger that translates after pulsed actuation of the displacement mechanism so as to increase pressure within the pump chamber and translate the delivery piston between the large diameter pump chamber and the small diameter pump chamber.

9. The insulin pump enclosure of claim 8 wherein the displacement mechanism comprises a solenoid.

\* \* \* \* \*